US012605300B2

(12) United States Patent
Kang et al.

(10) Patent No.: US 12,605,300 B2
(45) Date of Patent: Apr. 21, 2026

(54) DEVICE AND METHOD FOR PROVIDING VISUAL PERCEPTUAL TRAINING

(71) Applicants: THE ASAN FOUNDATION, Seoul (KR); UNIVERSITY OF ULSAN FOUNDATION FOR INDUSTRY COOPERATION, Ulsan (KR); NUNAPS INC., Seoul (KR)

(72) Inventors: Dong Wha Kang, Seoul (KR); Han A Kim, Seoul (KR); Rak Kyeun Hong, Guri-si (KR)

(73) Assignees: THE ASAN FOUNDATION, Seoul (KR); UNIVERSITY OF ULSAN FOUNDATION FOR INDUSTRY COOPERATION, Ulsan (KR); NUNAPS INC, Seoul (KR)

( * ) Notice: Subject to any disclaimer, the term of this patent is extended or adjusted under 35 U.S.C. 154(b) by 891 days.

(21) Appl. No.: 17/931,806

(22) Filed: Sep. 13, 2022

(65) Prior Publication Data
US 2023/0032569 A1     Feb. 2, 2023

Related U.S. Application Data

(63) Continuation of application No. PCT/KR2021/002972, filed on Mar. 10, 2021.

(30) Foreign Application Priority Data

Mar. 13, 2020     (KR) ........................ 10-2020-0031093

(51) Int. Cl.
*A61B 3/02*         (2006.01)
*A61B 3/00*         (2006.01)
(Continued)

(52) U.S. Cl.
CPC ............... *A61H 5/00* (2013.01); *A61B 3/032* (2013.01); *A61B 5/4088* (2013.01)

(58) Field of Classification Search
CPC .. A61B 3/02; A61B 3/00; A61B 3/102; A61B 3/1025; A61B 3/113; A61B 3/1015; A61B 3/1225; A61B 3/024; A61B 3/005
(Continued)

(56) References Cited

U.S. PATENT DOCUMENTS 6,876,758 B1     4/2005  Polat et al.
8,690,325 B1 *   4/2014  Straus .................. A61B 5/0002
                                                            351/200
(Continued)

FOREIGN PATENT DOCUMENTS

KR     10-2012-0107768 A     10/2012
KR         10-1534831 B1      7/2015
(Continued)

OTHER PUBLICATIONS

International Search Report issued in PCT/KR2021/002972; mailed Jun. 17, 2021.

*Primary Examiner* — Dawayne Pinkney
(74) *Attorney, Agent, or Firm* — Studebaker Brackett PLLC

(57)                    ABSTRACT

Disclosed is a device for providing visual perceptual training including an output module and a controller that controls the output module such that the output module outputs an instruction message informing a trainee of a rule related to visual perceptual training, provides a training session for the visual perceptual training, and stores a result in the training session for evaluating cognitive ability of the trainee, wherein the controller may, in the training session, control the output module such that the output module sequentially displays visual objects, check a type of a response of the trainee, determine whether the checked response is correct
(Continued)

Start

Output instruction message indicating rule related to perceptual training  ⟶ S1000

Provide training session for visual perceptual training  ⟶ S2000

Store result of determination in session for evaluating trainee's cognitive ability  ⟶ S3000

End according to the rule including the first condition and the second condition based on the attribute of the visual object, the display order of the visual object, and the type of the checked response, and output a feedback indicating that the checked response is correct.

19 Claims, 20 Drawing Sheets

(51) Int. Cl.

| | |
|---|---|
| *A61B 3/032* | (2006.01) |
| *A61B 3/10* | (2006.01) |
| *A61B 3/113* | (2006.01) |
| *A61B 5/00* | (2006.01) |
| *A61H 5/00* | (2006.01) |

(58) Field of Classification Search
USPC ....... 351/201, 205, 200, 206, 209, 210, 221, 351/222, 245, 246, 203, 223
See application file for complete search history.

(56) References Cited

U.S. PATENT DOCUMENTS

| | | | | |
|---|---|---|---|---|
| 2009/0281450 A1* | 11/2009 | Reichow | .................. | A61B 5/16 |
| | | | | 600/558 |
| 2016/0302710 A1* | 10/2016 | Alberts | ................ | A61B 5/1125 |
| 2017/0105666 A1* | 4/2017 | Lee | ........................... | G09B 7/06 |
| 2021/0259539 A1* | 8/2021 | Lewis | ................... | A61B 3/032 |

FOREIGN PATENT DOCUMENTS

| | | |
|---|---|---|
| KR | 10-2018-0041089 A | 4/2018 |
| KR | 10-2019-0111884 A | 10/2019 |

* cited by examiner

1100    Output module

1200    Input module

1300    Memory

1400    Communication module

Controller    1500

100

Start

Output instruction message indicating rule related to perceptual training          S1000

Provide training session for visual perceptual training          S2000

Store result of determination in session for evaluating trainee's cognitive ability          S3000

End

FIG. 3

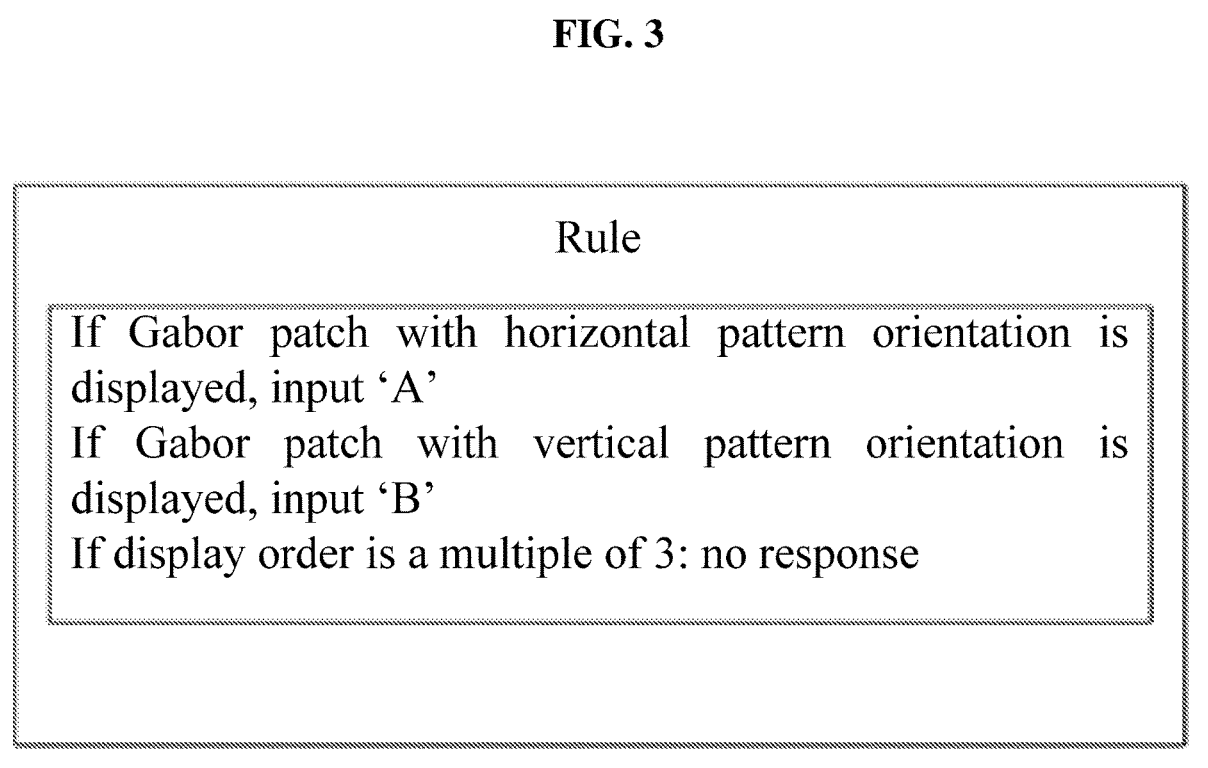

Rule

If Gabor patch with horizontal pattern orientation is displayed, input 'A'
If Gabor patch with vertical pattern orientation is displayed, input 'B'
If display order is a multiple of 3: no response

FIG. 6

| Order | 1 | 2 | 3 | 4 | 5 | 6 | 7 |
|---|---|---|---|---|---|---|---|
| Display | | | | | | | |
| Requested response | First Response | Second Response | Third Response | First Response | First Response | Third Response | Second Response |
| Response | First Response | Second Response | Third Response | First Response | First Response | Second Response | Second Response |
| Correct/ Incorrect | Correct | Correct | Correct | Correct | Correct | Incorrect | Correct |

FIG. 8

| Order | 1 | 2 | 3 | 4 | 5 | 6 |
|---|---|---|---|---|---|---|
| Test object | | | | | | |
| Requested response | First Response | Third Response | Second Response | Third Response | Third Response | Third Response |
| Response | First Response | Third Response | Third Response | Third Response | Third Response | First Response |
| Correct/ Incorrect | Correct | Correct | Correct | Correct | Correct | Incorrect |

FIG. 9

| Attributes of visual objects in preset previous order and present order are identical to each other | Attributes of visual objects in preset previous order and present order are different from each other |
|---|---|
| First response | Second response |

FIG. 10

| Order | 1 | 2 | 3 | 4 | 5 | 6 |
|---|---|---|---|---|---|---|
| Visual object | | | | | | |
| Visual object in second previous order | | | | | | |
| Requested response | | | Second Response | Second Response | First Response | Second Response |
| Response | | | Second Response | Second Response | Second Response | Second Response |
| Correct/ Incorrect | | | Correct | Correct | Incorrect | Correct |

Low    Middle    High (10%)    (50%)    (80%)

Motion coherence

DEVICE AND METHOD FOR PROVIDING VISUAL PERCEPTUAL TRAINING

CROSS-REFERENCE TO RELATED APPLICATIONS

The present application is a continuation of International Patent Application No. PCT/KR2021/002972, filed on Mar. 10, 2021, which is based upon and claims the benefit of priority to Korean Patent Application No. 10-2020-0031093 filed on Mar. 13, 2020. The disclosures of the above-listed applications are hereby incorporated by reference herein in their entirety.

BACKGROUND

Embodiments of the inventive concept described herein relate to a device and a method for providing visual perceptual training and more particularly, to a device and a method for providing visual perceptual training, which is for use in improving cognitive ability.

Interest in dementia, which mainly affects the elderly, is increasing as Korea became an aged society. Dementia refers to a state in which a patient's various cognitive abilities, including memory, are reduced due to impairment of brain function or old age, and the patient is unable to continue his or her daily life. Currently, as a method for improving the cognitive ability of dementia patients, there are various methods such as drug treatment, recall therapy, cognitive rehabilitation training, and visual perceptual training.

Visual perceptual training to improve cognitive ability stimulates areas around the hippocampus of the brain, which is responsible for the patient's spatial memory and cognitive functions. Through this, visual perceptual training improves the patient's cognitive abilities, including memory, based on brain plasticity. In this regard, there is a study that reported that 30 elderly people improved cognitive abilities including working memory after visual perceptual training (Adam Gazzaley et al. J Plos 2010).

However, the development of technology for providing visual perceptual training that is actually used to improve the cognitive ability of a patient is still insignificant.

SUMMARY

Embodiments of the inventive concept provide a device and a method for providing visual perceptual training using visual perceptual training that requires a cognitive load.

Embodiments of the inventive concept provide a device and a method for providing visual perceptual training using visual perceptual training combined with navigation.

However, problems to be solved by the inventive concept are may not be limited to the above-described problems. Although not described herein, other problems to be solved by the inventive concept can be clearly understood by those skilled in the art from the following description.

According to an embodiment, a method for providing visual perceptual training for improving cognitive ability, the visual perceptual training being performed by a visual perceptual training device, includes outputting an instruction message informing a trainee of a rule related to the visual perceptual training, providing a training session for the visual perceptual training, and storing a result in the training session for evaluating the cognitive ability of the trainee, wherein the providing of the training session includes sequentially displaying visual objects, checking a type of a response of the trainee, determining whether the checked response is correct according to the rule including a first condition and a second condition based on an attribute of the visual object, a display order of the visual object, and the type of the checked response, and outputting a feedback indicating that the checked response is correct, wherein the first condition is to provide an identification task to the trainee in the training session, and request, from the trainee, a first response when the visual object having a first attribute is displayed and a second response when the visual object having a second attribute is displayed, wherein the second condition is to provide a cognitive task together with the identification task such that the training session requests a cognitive load from the trainee, and when the order of the displayed visual objects is a predetermined number, request a third response from the trainee, and wherein the second condition have a higher priority than the first condition.

The first response and the second response may be a first type of user input and a second type of the user input, and the third response may be absence of the user input.

The attributes of the visual object may include at least one of existence or absence, contrast, size, shape, color, display time, brightness, movement, rotation, pattern, and depth.

The visual object may be related to a Gabor patch.

The predetermined number may include at least one of a multiple of N, a number that is not the multiple of N, a number whose remainder is M when divided by N, a number whose remainder is not M when divided by N, a number whose last digit is the multiple of N, a number whose last digit is not the multiple of N, and any one of three different numbers whose last digit is less than 10, N may be a natural number greater than 2, and M may be a natural number different from N.

The training session may be provided in a background image comprising a virtual vehicle for navigation and a virtual road.

The first response may be related to movement of the vehicle in a first orientation, the second response may be related to movement of the vehicle in a second orientation and the third response may be related to movement of the vehicle in a third direction. The training session may request an additional response related to movement of the vehicle. The background image may include an obstacle that prevents the movement of the vehicle and, the additional response may be related to steering the vehicle such that the vehicle is not to collide with the obstacle.

According to an embodiment, the inventive concept further include a computer-readable recording medium storing a program for executing the method of providing visual perceptual training according to the inventive concept in combination with a computer which is hardware.

According to an embodiment, a device for providing visual perceptual training includes an output module and a controller that controls the output module such that the output module outputs an instruction message informing a trainee of a rule related to visual perceptual training, provides a training session for the visual perceptual training, and stores a result in the training session for evaluating cognitive ability of the trainee, wherein the controller may, in the training session, control the output module such that the output module sequentially displays visual objects, check a type of a response of the trainee, determine whether the checked response is correct according to the rule including a first condition and a second condition based on an attribute of the visual object, a display order of the visual object, and the type of the checked response, and output a feedback indicating that the checked response is correct, wherein the first condition is to provide an identification task to the trainee in the training session, and request, from the trainee, a first response when the visual object having a first attribute is displayed and a second response when the visual object having a second attribute is displayed, wherein the second condition is to provide a cognitive task together with the identification task such that the training session requests a cognitive load from the trainee, and when the order of the displayed visual objects is a predetermined number, request a third response from the trainee, and wherein the second condition have a higher priority than the first condition.

BRIEF DESCRIPTION OF THE FIGURES

FIG. 3 is a diagram showing an instruction message informing a rule related to visual perceptual training according to the inventive concept;

FIGS. 5 and 6 are diagrams showing a first example of a training session of the inventive concept;

FIGS. 7 and 8 are diagrams showing a second example of a training session of the inventive concept;

FIGS. 9 and 10 are diagrams showing a third example of a training session of the inventive concept;

DETAILED DESCRIPTION

Figure 1:
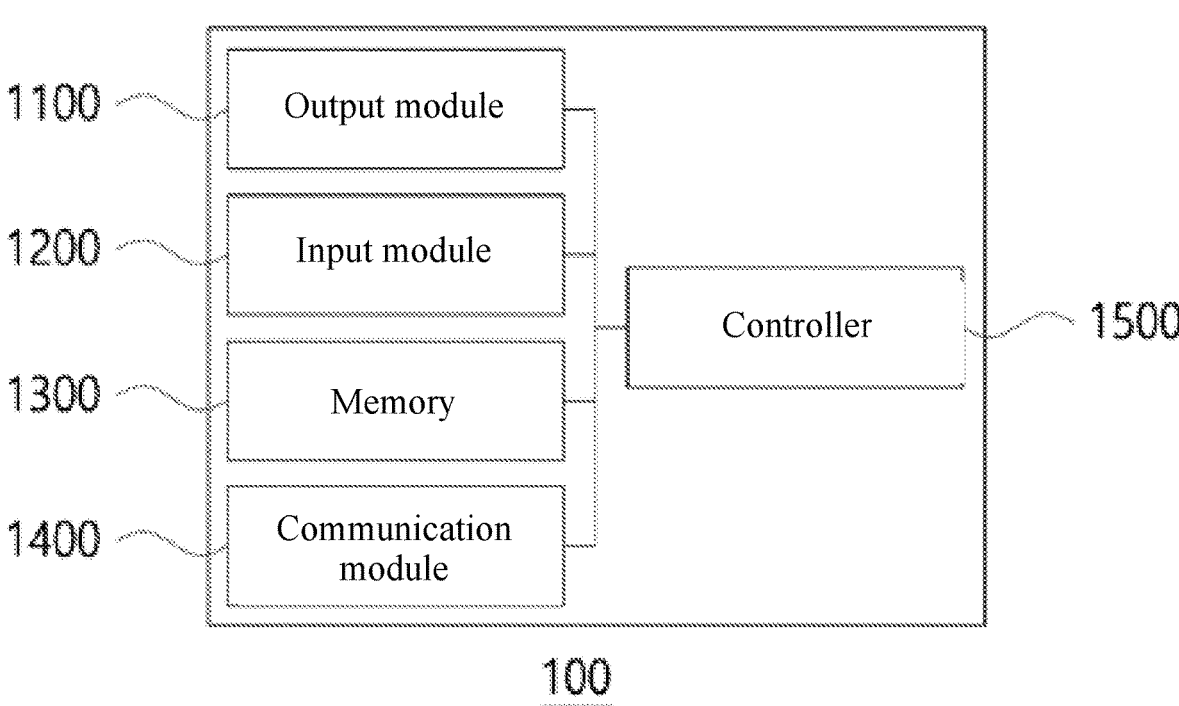
FIG. 1 is a block diagram of a device for providing visual perceptual training according to an inventive concept.

Advantages and features of the inventive concept and methods for achieving them will be apparent with reference to embodiments described below in detail in conjunction with the accompanying drawings. However, the inventive concept is not limited to the embodiments disclosed below, but can be implemented in various forms, and these embodiments are to make the disclosure of the inventive concept complete, and are provided so that this disclosure will be thorough and complete and will fully convey the scope of the invention to those of ordinary skill in the art, which is to be defined only by the scope of the claims.

The terminology used herein is for the purpose of describing particular embodiments only and is not intended to be limiting of the inventive concept. The singular expressions include plural expressions unless the context clearly dictates otherwise. In this specification, the terms "comprises" and/ or "comprising" are intended to specify the presence of stated elements, but do not preclude the presence or addition of elements. Like reference numerals refer to like elements throughout the specification, and "and/or" includes each and all combinations of one or more of the mentioned elements. Although "first", "second", and the like are used to describe various components, these components are of course not limited by these terms. These terms are only used to distinguish one component from another. Thus, a first element discussed below could be termed a second element without departing from the teachings of the inventive concept.

As used herein, the word "exemplary" means "serving as an example, instance, or illustration." Any implementation described herein as "exemplary" is not necessarily to be construed as preferred or advantageous over other implementations.

The term "unit, as used herein, means, but is not limited to, a software or hardware component, such as a Field Programmable Gate Array (FPGA) or an Application Specific Integrated Circuit (ASIC), which performs certain tasks. However, "~ unit" is not meant to be limited to software or hardware. "~ unit" may be configured to reside in an addressable storage medium or may be configured to reproduce one or more processors. As an example, "~ unit" may include components such as software components, object-oriented software components, class components and task components, processes, functions, attributes, procedures, sub-routines, segments of program codes, drivers, firmware, microcodes, circuitry, data, databases, data structures, tables, arrays, and variables. The functionality provided within elements and "parts" may be combined into a smaller number of elements and "parts" or further separated into additional elements and "parts."

Further, in this specification, all "units" may be controlled by at least one processor, and at least one processor may perform operations performed by "units" of the present disclosure.

Embodiments of the present specification may be described in terms of a function or a block performing a function. These blocks, which may be referred to herein as units or modules or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and/or software.

Embodiments of the present specification may be implemented using at least one software program running on at least one hardware device and may perform a network management function to control an element.

Unless otherwise defined, all terms (including technical and scientific terms) used herein have the same meaning as commonly understood by one of ordinary skill in the art to which this invention belongs. It will be further understood that terms such as those defined in commonly used dictionaries, will not be interpreted in an idealized or overly formal sense unless expressly so defined herein.

Spatially relative terms, such as "below", "beneath", "lower", "above", and "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. Components may also be oriented in other orientations, and thus spatially relative terms may be interpreted according to orientations.

As used herein, perceptual training refers to training to improve perception for stimulus through repetitive stimulus. In other words, in the present specification, the visual perceptual training refers to training to improve the perception for visual stimulus through repetitive training that provides the visual stimulus. Visual perceptual training should be broadly interpreted to include training to improve the ability to identify objects from stimuli incoming from the outside through the visual organ, as well as training to improve the ability to discover objects from the stimuli.

As used herein, cognition means any mental activity or state related to knowing, and cognition should be broadly interpreted to include perception, attention, memory, imagination, language function, problem-solving ability, and the like. In addition, as used herein, cognitive ability means a wide range of intellectual activity abilities required to perform all kinds of tasks ranging from simple to complex, and should be broadly interpreted to include memory, attention, imagination, language skills, problem-solving skills, judgment, learning skills, computational skills, spatial perception and comprehension, and the like.

As used herein, the expression "task" may refer to a goal and/or purpose to be achieved by a user. For example, a computerized task may be rendered using computerized components, and a user may be instructed as to a goal or purpose for performing the computerized task. A task may require an individual to provide or withhold a response to a particular stimulus.

As used herein, the expression "session" may refer to a time period, having a beginning and an end, during which a user interacts with a device to receive treatment from the device. For example, a session may be 1 second, 30 seconds, 1 minute, 1 hour, 12 hours, a day, a week, a month, or the like. Hereinafter, embodiments of the present disclosure will be described with reference to the accompanying drawings.

FIG. 1 is a block diagram of a device for providing visual perceptual training according to an inventive concept;

Referring to FIG. 1, a device 100 may include an output module 1100, an input module 1200, a memory 1300, a communication module 1400, and a controller 1500.

According to an embodiment, the device 100 may provide perceptual training for improving the cognitive ability of a trainee.

The sensory regions of the cerebral cortex receive and process signals from sensory organs including body sensory such as touch and pain, and sight, hearing, taste, and smell to allow the sensory to be recognized and perceived. When there is a problem in one of these pathways, perception of a relevant sensory may become impossible. Specifically, in the process of a person's recognition of a sensory stimulus (e.g., a visual stimulus), a sensory stimulus (e.g., a visual stimulus) is input to a sensory organ (e.g., an eye) to perform sensation, and the sensory area of the cerebrum (e.g., the visual cortex) performs perception to perform the recognition of deriving meaning by associating sensory representations (e.g., visual representations) with memory representations.

This sensory information is converted from short-term memory to long-term memory by the hippocampus, which plays an important role in learning and memory in connection with human cognitive ability. Specifically, the hippocampus processes intellectual, emotional, and factual information, and stores sensory information received from the sensory cortex for a short period of time, then transfers the sensory information to other parts of the brain and stores the sensory information as long-term memory or deletes the sensory information. That is, the hippocampus has close brain connectivity with the sensory cortex (e.g., the visual cortex).

Accordingly, as a method for improving a person's cognitive ability, a method of continuously stimulating the hippocampus by continuously providing sensory stimulation may be used. Specifically, based on the close brain connection between the hippocampus and the sensory cortex, when a person performs perceptual training in which sensory stimuli are continuously given, the hippocampus itself or its surroundings are continuously stimulated, and thus cognitive ability can be improved. Accordingly, the device 100 according to an embodiment may improve the cognitive ability of the trainee by providing perceptual training (e.g., visual perceptual training).

Hereinafter, for convenience, the device 100 provides a training session for visual perceptual training, but the device 100 provides a training session for auditory perception training, tactile perception training, etc. using other sensory stimuli. For example, for perceptual training, the device 100 does not display a visual object that is a visual stimulus, but a perceptual stimulus including at least one of a visual stimulus, an auditory stimulus, a gustatory stimulus, a tactile stimulus, and an olfactory stimulus. Here, each perceptual stimulus may have a specific attribute.

In the present specification, a specific attribute related to a stimulus may mean characteristics that the stimulus may have. For example, the attribute of the auditory stimulus may include at least one of intensity, speed, pitch, rhythm, and length of sound.

The device 100 may include various devices capable of performing computational processing. For example, the device 100 may include a desktop PC, a mobile phone, a smart phone, a laptop computer, personal digital assistants (PDA), a portable multimedia player (PMP), a slate PC, a tablet PC, an ultrabook, a wearable device, and the like.

According to an embodiment, the deice 100 may be worn on any part of the body and used in such a way that the output module 1100 faces a user's eyes. For example, the device 100 may include a head mounted device, such as a head mounted display (HMD) mounted on a user's head to display a video, smart glasses, and smart goggles, or a display device such as a mobile phone used while mounted on a head-mounted device, or the like.

The output module 1100 may output a video or an image. For example, the output module 1100 may include an LCD, an OLED, an AMOLED display, and the like. Here, when the output module 1100 is provided as a touch screen, the output module 1110 may perform the function of the input module 1200. In this case, the separate input module 1200 may not be provided according to selection, and the input module 1200 capable of performing limited functions such as volume control, power button, and home button may be provided. As another example, the output module 1100 may be provided in the form of an image output port for transmitting image information to an external display device.

Also, the output module 1100 may display an image for visual perceptual training of a user. For example, the output module 1100 may visually output a process before starting a training session, an instruction, an image for performing the training session, and the like.

According to an embodiment, the screen of the output module 1100 may include a first display part corresponding to the left eye of a patient and a second display part corresponding to the right eye of the patient. Here, the first display part may output a first image, the second display part may output a second image, and the controller 1500 may adjust the distance between the first image and the second image, the degree of overlap, and the like to adjust the parallax, focus, or the like of images provided to a user.

Also, the output module 1100 may output information to be provided to the user in various ways. For example, the output module 1100 may include a speaker, a motor, a haptic device, a vibrator, a signal output circuit, and the like, and may be a module that outputs various stimuli.

Also, the output module 1100 may audibly or tactilely output information for the visual perceptual training. Specifically, the output module 1100 may output an alarm indicating the start and end of a training session in an audible or tactile manner.

According to an embodiment, the output module 1100 may output a stimulus for other perceptual training (e.g., auditory perceptual training). For example, the output module 1100 may output, but not limited thereto, an auditory stimulus for auditory perceptual training Specifically, the output module 1100 may output an instruction message informing a rule related to auditory perceptual training and an auditory stimulus for auditory perceptual training.

The input module 1200 may obtain a signal corresponding to a user input. For example, the input module 1200 may receive a user input for performing a training session, a user input for adjusting the focus of an image for the training session during the training session, and a user input for receiving a user response requested by the training session, or the like.

Also, the input module 1200 may include a keyboard, a key pad, a button, a jog shuttle, a wheel, and the like. In addition, the user input in the input module 1200 may be, for example, a press of a button, a touch, and a drag. Also, when the output module 1100 is implemented with a touch screen, the output module 1100 may serve as the input module 1200.

According to an embodiment, the input module 1200 may be configured as a separate module connected to the device 100 wirelessly or by wire. For example, the device 100 may provide an image for the training session to a user through the output module 1100 mounted on and attached to the user's head, and receive an input related to the training session from the user through the input module 1200 configured as a separate module given to the user's hand.

The memory 1300 may store various types of data. For example, the memory 1300 may store data related to a visual perceptual training. Specifically, the memory 1300 may store a program for executing a training session, user information (e.g., user personal information, a user's response when the training session is performed, the result of a user's training session), cognitive ability test result, and the like.

Also, the memory 1300 may include at least one type of storage medium among a flash memory type, a hard disk type, a multimedia card microtype, a card type memory (e.g., SD or XD memory), random access memory (RAM), static random access memory (SRAM), read-only memory (ROM), electrically erasable programmable read-only memory (EEPROM) programmable read-only memory (PROM), magnetic memory, magnetic disk, and optical disk. In addition, the memory 1300 may temporarily, permanently, or semi-permanently store information, and may be provided as a built-in or removable type.

The communication module 1400 may communicate with an external device. For example, the communication module 1400 may communicate with a server (not shown). Specifically, the communication module 1400 may transmit data related to a user's visual perceptual training to the server, and may receive a personalized feedback therefor from the server.

Also, the communication module 1400 may perform communication according to wired and wireless communication standards. For example, the communication module 1400 may include a mobile communication module for BLE (Bluetooth Low Energy), Bluetooth, WLAN (Wireless LAN), WiFi (Wireless Fidelity), WiFi Direct, NFC (Near Field Communication), Infrared Data Association (IrDA), UWB (Ultra Wide Band), Zigbee, 3G, 4G or 5G, and a wired/wireless module for transmitting data through various other communication standards.

The controller 1500 may control each element of the device 100 or process and calculate various types of information. For example, the controller 1500 may output an image for the training session through the output module 1100. Specifically, the controller 1500 may output an instruction message informing a rule related to visual perceptual training and a visual object for visual perceptual training on a screen through the output module 1100.

The controller 1500 may be implemented by software, hardware, or a combination thereof. For example, in hardware, the controller 1500 may be implemented with a field programmable gate array (FPGA), an application specific integrated circuit (ASIC), a semiconductor chip, or other various types of electronic circuits. Also, for example, in software, the controller 1500 may be implemented in a logic program executed according to the above-described hardware or in various computer languages.

In the following description, unless otherwise stated, it may be understood that the operation of the device 100 is performed under the control of the controller 1500.

The device 100 illustrated in FIG. 1 is merely an example, and the configuration of the device 100 is not limited thereto. For example, the device 100 may include a server connected to the device 100 through wired/wireless communication to store data related to the user's visual perceptual training.

In addition, a function performed by each component of the device 100 does not necessarily have to be performed by the corresponding component and may be performed by another component. For example, although it has been described that the memory 1300 of the device 100 stores data related to the user's visual perceptual training, a server connected to the device 100 through wired/wireless communication may store data related to the visual perceptual training of a user.

Figure 2:
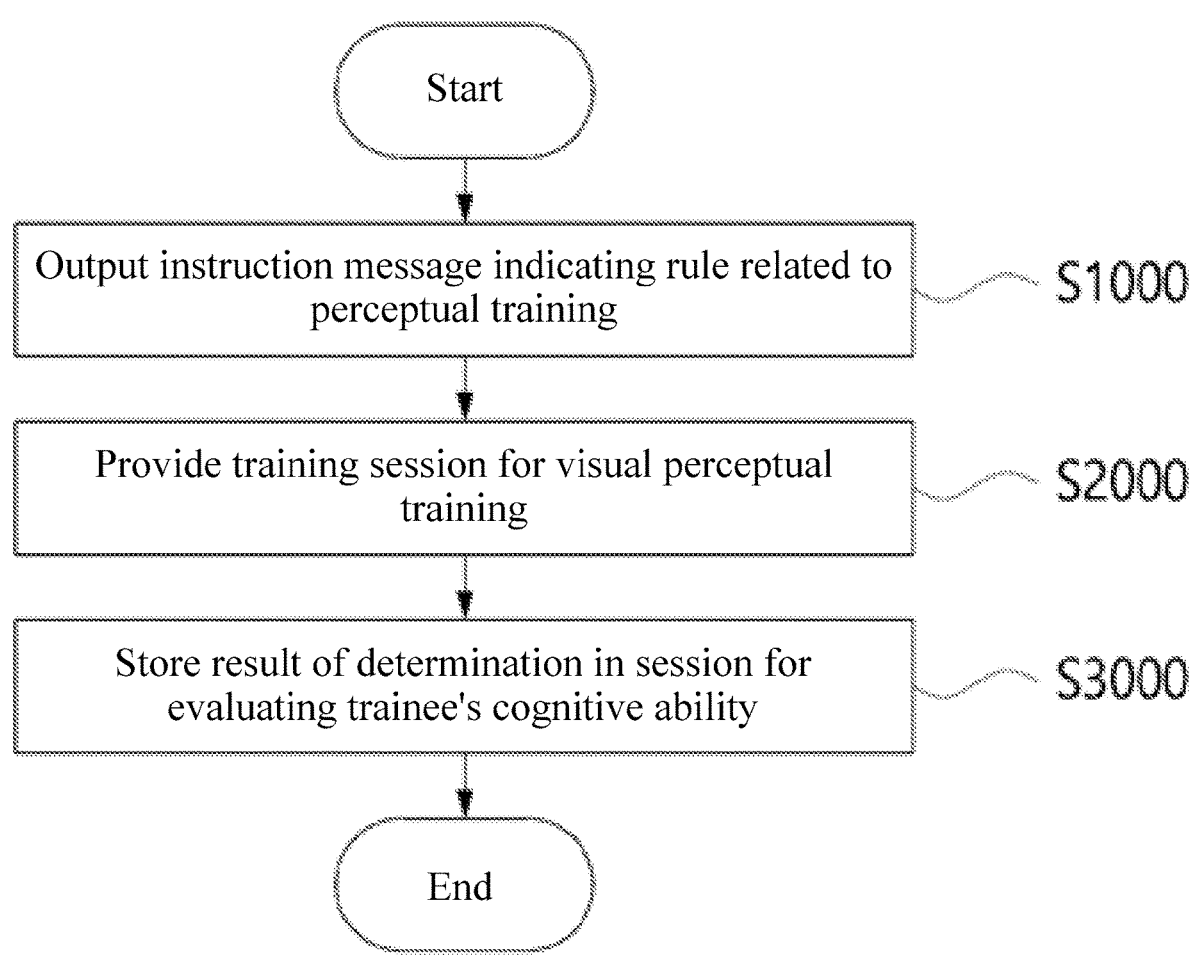
FIG. 2 is a flowchart of a method for providing visual perceptual training according to the inventive concept.

FIG. 2 is a flowchart of a method for providing visual perceptual training according to an embodiment.

Referring to FIG. 2, the method for providing visual perceptual training according to an embodiment may include outputting an instruction message informing a rule related to visual perceptual training (S1000), providing a training session for visual perceptual training (S2000), and storing the result of determination in a session for evaluating the cognitive ability of a trainee (S3000).

According to an embodiment, the device 100 may output an instruction message informing of a rule related to visual perceptual training (S1000).

The rule related to the visual perceptual training may be a rule regarding an identification task provided during the training session. For example, the rule related to visual perceptual training may be a rule for identifying visual objects sequentially displayed and requiring a correct response from a trainee. Specifically, the rule related to visual perceptual training may be a rule for requiring a first response when a first visual object is displayed and requiring a second response when a second visual object is displayed.

In addition, the rule related to the visual perceptual training may be a rule for requesting a cognitive load from the trainee with an identification task provided during a training session. For example, a rule related to visual perceptual training may be a rule requesting a trainee not to respond to a visual object in a specific order based on the order of visual objects sequentially displayed. For another example, a rule related to visual perceptual training may be a rule requesting a trainee to compare a displayed visual object with a visual object displayed before a specific order.

It is noted that the rules for requesting a cognitive load from the trainee are not limited to the above-described rules, and may be a rule for requesting a cognitive load related to memory, attention, executive function, language, or the like from the trainee.

The controller 1500 may output an instruction message indicating a rule to be applied during the training session through the output module 1100. For example, the controller 1500 may display, through the output module 1100, an instruction message including a variety of content such as text, a drawing, and a video for describing rules to be applied to visual perceptual training. The instruction message may be information informing of rules related to visual perceptual training, such as including a tutorial of visual perceptual training and including a correct answer according to the user's tutorial performance.

It is noted that the device 100 may output the instruction message in another method, such as a method of outputting an instruction message indicating a rule to be applied during a training session in an audible manner through the output module 1100. In addition, rules related to visual perceptual training may be different for respective embodiments of a training session to be described later.

FIG. 3 is a diagram regarding an instruction message informing a rule related to visual perceptual training according to the inventive concept.

Referring to FIG. 3, the device 100 may output an instruction message describing at least one of rules related to an identification task provided during a training session and/or a rule for requesting a cognitive load. A user may need to input a correct input in consideration of the output instruction message.

For example, the device 100 may output an instruction message requesting input "A" from a user when a Gabor patch with a horizontal pattern is displayed, an instruction message requesting input "B" from the user when a Gabor patch with a horizontal pattern is displayed, and an instruction message requesting no response from the user when the display order is a multiple of three. It is noted that the output instruction message is not limited to the output of a sentence as shown in FIG. 3, and a variety of content such as a drawing and a video may be output.

According to an embodiment, the device 100 may provide a training session for visual perceptual training (S2000).

For example, the controller 1500 may provide a training session by displaying a visual object (e.g., Gabor patch) through the output module 1100 for visual perceptual training of the trainee, and for requesting a response related to the identification of the displayed visual object from a user. Here, the controller 1500 may request a response to a rule related to visual perceptual training from the user to improve the trainee's cognitive ability.

Figure 4:
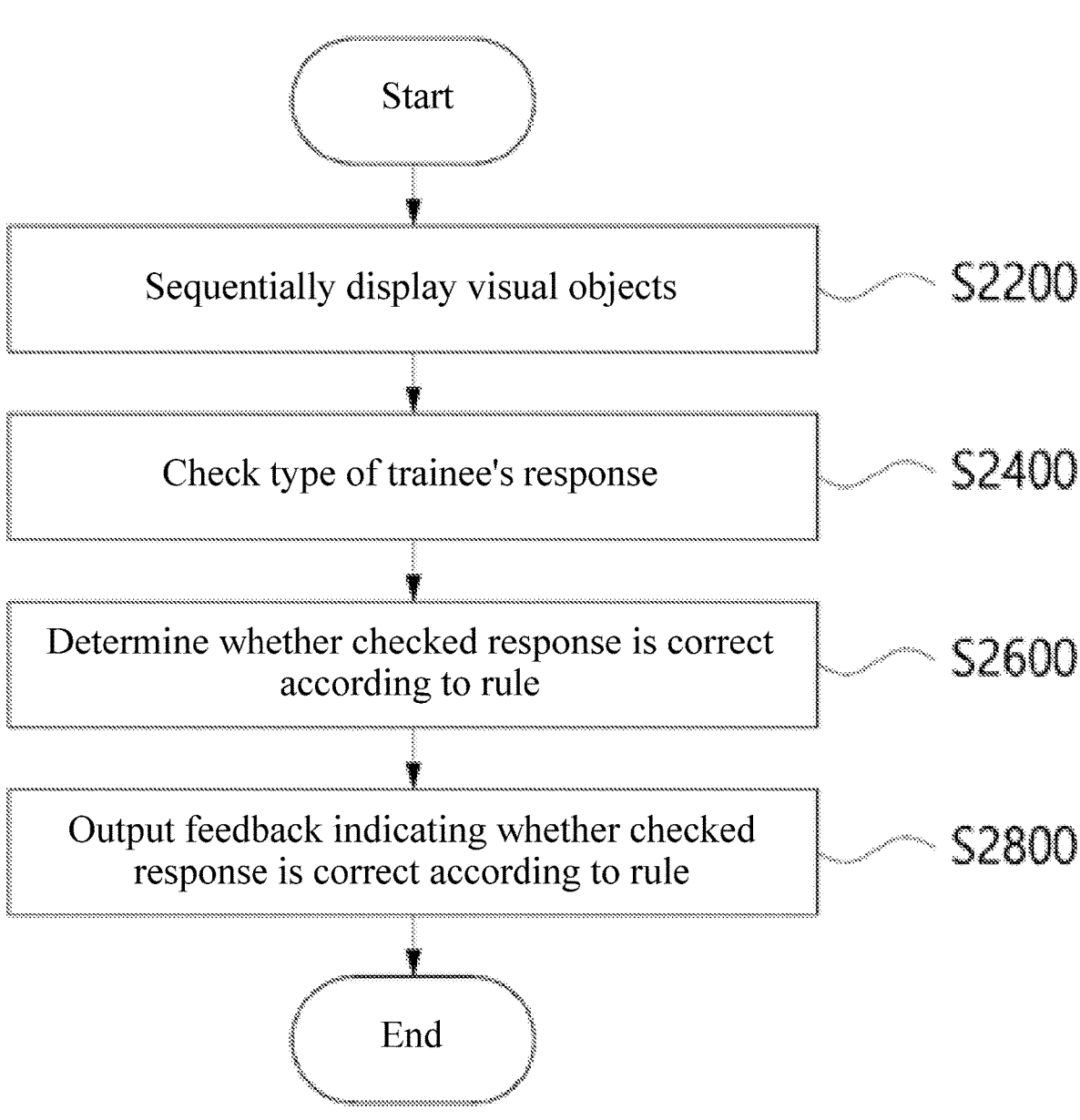
FIG. 4 is a flowchart of a method for providing a training session according to the inventive concept.

FIG. 4 is a flowchart of a method for providing a training session according to the inventive concept.

Referring to FIG. 4, a method of providing a training session according to an embodiment may include sequentially displaying visual objects (S2200), checking the type of a trainee's response (S2400), determining whether or not the checked response is correct based on a rule (S2600) and outputting a feedback indicating whether the checked response is correct (S2800).

According to an embodiment, the device 100 may sequentially display visual objects on a screen to provide an identification task to a trainee in a training session (S2200).

The controller 1500 may display the visual objects through the output module 1100 and request a response for identifying the displayed visual object from a user. For example, the controller 1500 may request a response corresponding to each of the displayed visual objects from the user.

Also, the controller 1500 may display a visual object through the output module 1100 and request a response for identifying a visual object different from the displayed visual object from the user. For example, the controller 1500 may request, from the user, a response that identifies an attribute of the displayed visual object, which is different from the attribute of the displayed visual object. Here, another visual object may be changed based on rules related to visual perceptual training.

The visual object may be provided in various forms, such as a two-dimensional form or a three-dimensional form. For example, the first visual object may include a character, a figure, a Gabor patch, or the like, but not limited thereto.

According to an embodiment, the controller 1500 may provide the visual object as a Gabor patch in which the orientation, angle, brightness, or the like of the stripes are variously adjusted. For example, the controller 1500 may provide a visual object as a Gabor patch having vertical or horizontal stripes. A Gabor patch is a patch using a series of differences of Gaussians (DOG) stimuli, which appear as blurred lines, as a pattern made of dark and light stripes in a desired orientation and at a desired angle. In general, the Gabor patch is treated as patterns that are optimized to stimulate unused human photoreceptors. Therefore, the device 100 may improve the effect of the trainee's visual perceptual training by displaying the Gabor patch.

Also, a visual object may have a specific attribute, such as rotating in a specific orientation. Here, the attributes of the visual object may be, for example, but not limited to, contrast, color, size, display time, brightness, movement, rotation, pattern, depth, and the like.

For example, the visual object may be a Gabor patch having a specific attribute. For example, the attributes of the Gabor patch may be, but not limited to, a pattern frequency, a pattern orientation, a pattern width, a pattern contrast, or the like.

According to an embodiment, the device 100 may check the type of a trainee's response (S2400).

For example, the controller 1500 may obtain the trainee's response related to the displayed visual object from the input module 1200. Specifically, the controller 1500 may check what type of response the obtained trainee's response is. Here, each type of response may correspond to each displayed visual object.

For example, the controller 1500 may request, from the user, a response with a first type (for example, input of a left button of the input module 1200) when a first visual object is displayed, and request, from the user, a response with a second type (for example, input of a right button of the input module 1200) when a second visual object is displayed. It is noted that each type of response may correspond to an attribute of each displayed visual object.

As another example, the controller 1500 may obtain a trainee's response related to a given rule from the input module 1200. Specifically, the controller 1500 may check what type of response the obtained trainee's response is.

Also, the types of responses include various types of user inputs, and the absence of a user input may be one of the types of responses.

According to an embodiment, the device 100 may determine whether the checked response is correct according to the rule (S2600).

The controller 1500 may determine whether the checked response is correct according to the rule based on the displayed visual object and the type of the checked response. For example, the controller 1500 may compare the type of a response corresponding to the displayed visual object with the type of a checked response, and when the two types of responses are the same, determine that the checked response is correct.

According to an embodiment, the device 100 may output a feedback indicating whether the checked response is correct (S2800).

The controller 1500 may output a feedback indicating whether the checked response is correct through the output module 1100. For example, the controller 1500 may display a message, a video, an image, or the like regarding whether the checked response is correct, through the output module 1100.

As another example, the controller 1500 may audibly output a voice, a sound, an alarm, or the like regarding whether the checked response is correct, through the output module 1100.

As another example, the controller 1500 may output various types of vibrations regarding whether the checked response is correct through the output module 1100 in a tactile manner.

Specific embodiments of the visual perceptual training provided in step S2000 will be described later.

According to an embodiment, the device 100 may store the result of the determination within the training session for evaluating the trainee's cognitive ability (S3000).

The controller 1500 may store, in the memory 1300, the result of the determination regarding whether the trainee's response in the training session is correct. For example, the controller 1500 may store, in the memory 1300, the total number of responses, the number of correct responses, the number of incorrect responses and the like in the training session.

The controller 1500 may evaluate the cognitive ability of the trainee. For example, the controller 1500 may evaluate the cognitive ability of the trainee based on the result of the determination in the training session. Specifically, the controller 1500 may evaluate the cognitive ability of the trainee as being higher as the higher the ratio of the number of correct responses to the number of incorrect responses in the training session.

As another example, the controller 1500 may evaluate the cognitive ability of the trainee based on the difficulty of visual perceptual training in a performed training session. Specifically, the controller 1500 may evaluate the cognitive ability of the trainee as being improved when a second training session has a higher degree of difficulty even though the results of the first training session and the second training session performed thereafter are the same.

In addition, the method for providing visual perceptual training according to the inventive concept may further include adjusting the difficulty of visual perceptual training in the training session.

The controller 1500 may determine the difficulty of visual perceptual training in the training session based on the trainee's response. For example, the controller 1500 may increase the difficulty of visual perceptual training in the training session when the trainee's responses to the visual object are correct or consecutively correct. For another example, the controller 1500 may decrease the difficulty of visual perceptual training in the training session when the trainee's responses are incorrect or are consecutively incorrect.

Also, the device 100 may switch screens providing the visual perceptual training to increase or decrease the difficulty of visual perceptual training in the training session. For example, the controller 1500 may change visual objects to be displayed to increase or decrease the difficulty of visual perceptual training in the training session. Specifically, the controller 1500 may change the attribute (e.g., existence or absence, contrast, size, shape, display time, brightness, movement, rotation, pattern, depth, or the like) of a displayed visual object to increase or decrease the difficulty of visual perceptual training in the training session.

According to the inventive concept, the controller 1500 may adjust the difficulty of visual perceptual training in the training session by changing the contrast of the displayed visual object. For example, the controller 1500 may increase the difficulty of visual perceptual training by lowering the contrast of the displayed visual object.

According to the inventive concept, the controller 1500 may adjust the difficulty of visual perceptual training in the training session by changing the size of the displayed visual object. For example, the controller 1500 may increase the difficulty of visual perceptual training by decreasing the size of the displayed visual object.

According to the inventive concept, the controller 1500 may adjust the difficulty of visual perceptual training in the training session by changing the display time of a visual object. For example, the controller 1500 may increase the difficulty of visual perceptual training by decreasing the display time of the visual object.

Of course, the device may adjust the difficulty of visual perceptual training in the training session in various methods such as changing the brightness, saturation, and size of a screen that provides visual perceptual training, or changing the number of displayed visual objects to adjust the difficulty, without being limited to the above-described method. For example, the device 100 may increase the number of displayed visual objects to increase the difficulty of visual perceptual training in the training session.

Hereinafter, various embodiments of a training session for visual perceptual training provided by the device 100 will be described.

First Example

Hereinafter, a first example of a training session provided by the device 100 will be described.

Figure 5:
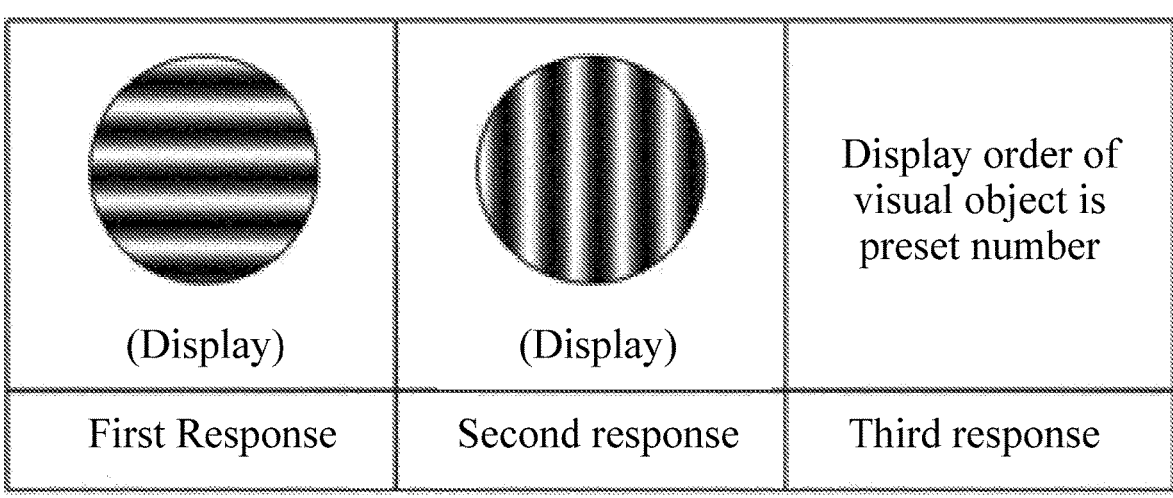

FIGS. 5 and 6 are diagrams showing a first example of a training session of the inventive concept.

Referring to FIG. 5, the device 100 may display a visual object in a training session according to a first example and request various types of responses according to a rule.

The rule related to visual perceptual training in the training session according to the first example may include a first condition and a second condition. Accordingly, a trainee may need to input a correct response according to the visual perceptual training based on the first condition and the second condition.

The first condition is to provide an identification task to the trainee in the training session, wherein the trainee is requested to identify a displayed visual object, and input a correct response according to the first condition.

The first condition may be a condition for requesting a first response from the trainee when the device 100 displays a visual object having a first attribute. For example, when the device 100 displays a Gabor patch having a horizontal pattern orientation, the first condition may be a condition for requesting a first type of user input (e.g., the input of the left button of the input module 1200) from the trainee.

Also, the first condition may be a condition for requesting a second response from the trainee when the device 100 displays a visual object having a second attribute. For example, when the device 100 displays a Gabor patch having a vertical pattern orientation, the first condition may be a condition for requesting a second type of user input (e.g., the input of the right button of the input module 1200) from the trainee.

The second condition is to provide a cognitive task along with an identification task such that the training session requests a cognitive load from the trainee, the trainee may need to remember the order of the displayed visual objects and input a correct response according to the second condition. The second condition may have a higher priority than the first condition.

The second condition may be a condition for requesting a third response from the trainee when the order of the visual objects sequentially displayed by the device 100 is a predetermined number. For example, the device 100 may request the absence of user input from the trainee when the order of sequentially displayed Gabor patches is a multiple of 3. It is noted that the type of response requested by the device 100 may be changed according to rules related to visual perceptual training, such as requesting a third type of user input, instead of requesting the absence of user input from the trainee.

Also, the predetermined number of the second condition may be a result value according to a simple formula. For example, when N is a natural number greater than 2, and M is a natural number different from N, the predetermined number of the second condition may include at least one of a multiple of N, a number that is not the multiple of N, a number whose remainder is M when divided by N, a number whose remainder is not M when divided by N, a number whose last digit is the multiple of N, a number whose last digit is not the multiple of N, and any one of three different numbers whose last digit is less than 10. Of course, the predetermined number of the second condition may be determined in other methods such as a method of arbitrarily selecting a number instead of the result value according to the formula.

According to an embodiment, the device 100 may change the difficulty of visual perceptual training in the training session. For example, the controller 1500 may change the difficulty of visual perceptual training in the training session by changing a time period during which the visual object is displayed.

Referring to FIG. 6, the device 100 may sequentially display a Gabor patch with a horizontal pattern orientation or a Gabor patch with a vertical pattern orientation in the training session according to the first example. Here, the rule related to visual perceptual training may be a rule for requesting, from the trainee, a first response when displaying a Gabor patch with a horizontal pattern orientation, a second response when displaying a Gabor patch with a vertical pattern orientation, and a third response when the order of displayed visual objects is a multiple of 3.

The device 100 may request the trainee to respond to a rule related to visual perceptual training. For example, the device 100 may request a response from the trainee in a training session, the response corresponding to "order 1: first response, order 2: second response, order 3: third response, order 4: first response, order 5: first response, order 6: third response, order 7: second response."

The device 100 may check the trainee's response in the training session. For example, the device 100 may receive and check a response from the trainee, the response including "order 1: first response, order 2: second response, order 3: third response, order 4: first response, order 5: first response, order 6: second response, order 7: second response."

The device 100 may determine whether the checked response is correct. For example, the device 100 may determine whether the checked response is correct according to a rule including the first condition and the second condition based on the attribute of the visual object, the display order of the visual object, and the type of the checked response.

Referring to FIG. 6, the device 100 may request a first response from the trainee because a Gabor patch displayed in order 1 is a Gabor patch with a horizontal pattern orientation, and when the checked response is the first response, determine that the checked response is correct. Also, the device 100 may request a second response from the trainee because a Gabor patch displayed in order 2 is a Gabor patch with a vertical pattern orientation, and when the checked response is the second response, determine that the checked response is correct. Further, the device 100 may request a third response from the trainee because the order 6 in which the Gabor patch is displayed is the multiple of 3, and when the checked response is the second response, determine that the checked response is incorrect. That is, the device 100 may determine whether the checked response is correct or incorrect (right or wrong), such as "order 1: correct, order 2: correct, order 3: correct, order 4: correct, order 5: correct, order 6: incorrect, order 7: correct" in the training session.

It is noted that the training session according to the embodiment may be provided using other perceptual stimuli, but is not limited to the above description.

Second Example

Hereinafter, a training session according to a second example provided by the device 100 will be described.

Figure 7:
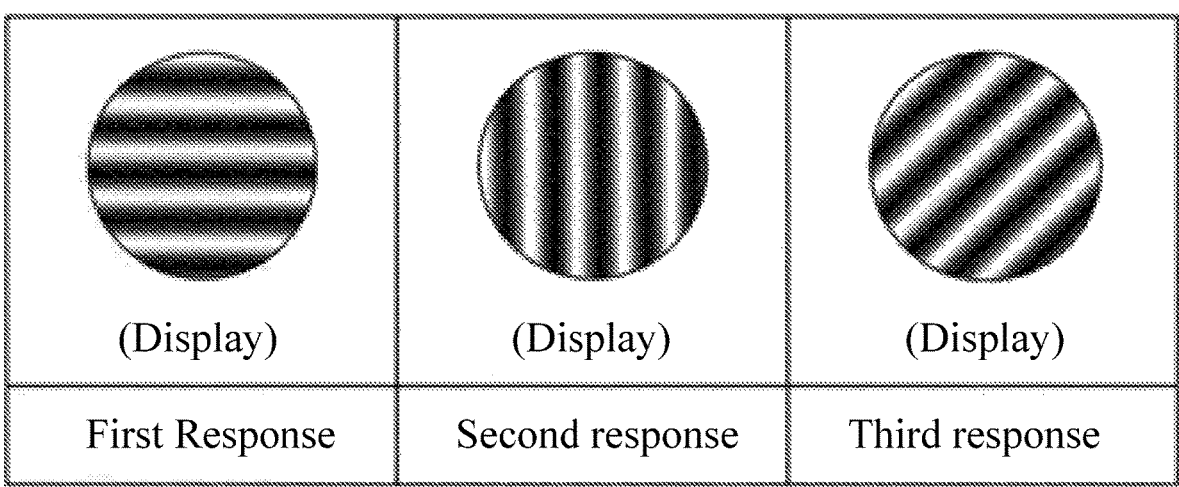

FIGS. 7 and 8 are diagrams showing a second example of a training session of the inventive concept.

Referring to FIG. 7, the device 100 may display a visual object in a training session according to a second example and request various types of responses according to a rule.

The rule related to the visual perceptual training of a training session according to the second example is to provide an identification task to a trainee in the training session, wherein the trainee needs to identify a test object having the test value of a displayed specific attribute, compare the test object with a reference object having a reference value of the specific attribute, and input a correct response. That is, the rule related to visual perceptual training may be a rule for requesting a specific type of response from a trainee when the displayed test object is identical to a preset reference object, and requesting a different type of response from the trainee when the displayed test object is different from the preset reference object.

According to an embodiment, the device 100 may request the first response when the displayed test object is identical to the first reference object. For example, the device 100 may request the first response from the trainee when the test value of the specific attribute of the displayed test object is identical to the first reference value of the specific attribute of the first reference object. Specifically, when the device 100 displays a Gabor patch having a horizontal pattern orientation, the device 100 may request a first type of user input (e.g., the input of the left button of the input module 1200) from the trainee.

According to an embodiment, the rule may be a rule for requesting a second response from the trainee when the displayed test object is identical to the second reference object. For example, the rule may be a rule requesting the second response from the trainee when the test value of the specific attribute of the displayed test object is identical to the second reference value of the specific attribute of the second reference object.

Specifically, when the device 100 displays a Gabor patch having a vertical pattern orientation, the rule may be a rule for requesting a second type of user input (e.g., the input of the right button of the input module 1200) from the trainee.

According to an embodiment, the rule may be a rule for requesting a third response from the trainee when the displayed test object is different from both the first reference object and the second reference object. For example, the rule may be a rule requesting a third response from the trainee when the test value of the specific attribute of the displayed test object is different from both the first reference value and the second reference value of the specific attributes of the first reference object and the second reference object. Specifically, the device 100 may request the absence of a user input from the trainee when displaying a Gabor patch having a pattern orientation inclined at a certain angle, except for the horizontal and vertical pattern orientations. Here, the degree of inclination of the pattern orientation of the Gabor patch may be determined based on the difficulty of visual perceptual training.

It is noted that the type of response requested by the device 100 may be changed according to rules related to visual perceptual training, such as requesting a third type of user input, instead of requesting the absence of user input from the trainee.

According to the inventive concept, the device 100 may request, from a trainee, a first response when the test value in the pattern orientation of a displayed test object is identical to a first reference value in the pattern orientation of a first reference object, a second response when the test value in the pattern orientation of the displayed test object is identical to a second reference value in the pattern orientation of a second reference object, and a third response when the test value in the pattern orientation of a displayed test object is different from the first reference value and the second reference value in the pattern orientations of the first reference object and the second reference object.

According to the inventive concept, the device 100 may change the difficulty of visual perceptual training in the training session. For example, the controller 1500 may change the difficulty of visual perceptual training in the training session based on a result of determining whether the checked response is correct. Specifically, the controller 1500 may increase the difficulty when the result of the determination is correct or consecutively correct, and decrease the difficulty when the result of the determination is incorrect or consecutively incorrect.

According to the inventive concept, the device 100 may adjust the difficulty of visual perceptual training by adjusting a difference between two reference objects and a third test object that is different from the two reference objects. For example, when the controller 1500 displays the third test object having the attribute of a test value that is different from the reference values of specific attributes of the two reference objects, the controller 1500 may change the difficulty by adjusting an average difference between one of the two reference values and the test value of the third test object. Here, the average difference may be smaller as the difficulty level is higher. Through this, the device 100 may request the trainee to more accurately memorize the reference object, thereby improving the trainee's cognitive ability.

According to the inventive concept, the device 100 may adjust the difficulty of visual perceptual training by changing a difference in pattern orientation between the two reference objects and a third test object that is different from the two reference objects. For example, the controller 1500 may decrease the difference between one of a first pattern orientation and a second pattern orientation and a third pattern orientation to increase the difficulty of visual perceptual training in the training session when displaying a third test object with a third pattern orientation different from both the first pattern orientation and the second pattern orientation, the first reference object being a Gabor patch with the first pattern orientation and the second reference object being a Gabor patch with the second pattern orientation.

According to the inventive concept, the device 100 may adjust the difficulty of visual perceptual training by changing a difference in pattern contrast between the two reference objects and a third test object that is different from the two reference objects. For example, the controller 1500 may decrease the difference between one of a first pattern contrast and a second pattern contrast and a third pattern contrast to increase the difficulty of visual perceptual training in the training session when displaying a third test object with the third pattern contrast different from both the first pattern contrast and the second pattern contrast, the first reference object being a Gabor patch with the first pattern contrast and the second reference object being a Gabor patch with the second pattern contrast.

According to the inventive concept, the device 100 may adjust the difficulty of visual perceptual training by changing a difference in pattern width between the two reference objects and a third test object that is different from the two reference objects. For example, the controller 1500 may decrease the difference between one of a first pattern width and a second pattern width and a third pattern width to increase the difficulty of visual perceptual training in the training session when displaying a third test object with the third pattern width different from both the first pattern width and the second pattern width, the first reference object being a Gabor patch with the first pattern width and the second reference object being a Gabor patch with the second pattern width.

Referring to FIG. 8, the device 100 may sequentially display Gabor patches having various pattern orientations as a test object having a test value (e.g., a horizontal or vertical pattern orientation) of a specific attribute (pattern orientation) in a training session according to the second example. Here, the first reference object may be a Gabor patch having a horizontal pattern orientation, and the second reference object may be a Gabor patch having a vertical pattern orientation.

The device 100 may request a response to a displayed test object from a trainee. For example, the device 100 may request a response from the trainee in a training session, the response corresponding to "order 1: first response, order 2: third response, order 3: second response, order 4: third response, order 5: third response, order 6: third response."

The device 100 may check the trainee's response in the training session. For example, the device 100 may receive and check a response from the trainee, the response including "order 1: first response, order 2: third response, order 3: second response, order 4: third response, order 5: third response, order 6: third response."

The device 100 may determine whether the checked response is correct. For example, the device 100 may determine whether a checked response is correct according to a rule based on the test value and the type of the checked response.

Referring to FIG. 8, the device 100 may request a first response from the trainee because a test object displayed in order 1 is a Gabor patch with a horizontal pattern orientation, and when the checked response is the first response, determine that the checked response is correct. Also, the device 100 may determine that the checked response is correct when a requested response is a third response and the checked response is the third response because the test object displayed in order 2 is a Gabor patch with an inclined pattern orientation. Also, the device 100 may determine that the checked response is incorrect when a requested response is the third response and the checked response is the first response because the test object displayed in order 6 is a Gabor patch with an inclined pattern orientation. That is, the device 100 may determine whether the checked response is correct or incorrect, such as "order 1: correct, order 2: correct, order 3: correct, order 4: correct, order 5: correct, order 6: incorrect" in the training session.

Also, the device 100 may adjust the difficulty of visual perceptual training by adjusting a difference between two reference objects and a third test object that is different from the two reference objects. Referring to FIG. 8, as the visual perceptual training proceeds from order 4 to order 6, it can be seen that the difference between the pattern orientation of the reference object and the pattern orientation of the test object is reduced, and thus the difficulty increases. Here, the difference between the pattern orientation of the test object and the pattern orientation of the first reference object is gradually reduced, and the difficulty gradually increases as the sequence proceeds to order 6.

It is noted that the training session according to the embodiment may be provided using other perceptual stimuli without being not limited to the above description.

Third Example

Hereinafter, a training session according to a third example provided by the device 100 will be described.

FIGS. 9 and 10 are diagrams showing a third example of a training session of the inventive concept.

Referring to FIG. 9, the device 100 may request various types of responses according to a rule in a training session according to a third example.

The rule related to the visual perceptual training of the training session according to the third example is to provide a trainee with an identification task and a cognitive task together in the training session, wherein the trainee needs to identify a displayed visual object, remember a visual object displayed in a previous specific order, and input a correct response. That is, the rule related to visual perceptual training may be a rule for comparing the displayed visual object with a visual object displayed in a preset previous order and requesting a correct response from the trainee.

According to the inventive concept, the rule related to visual perceptual training may be a rule for requesting a first response from the trainee when a first attribute of a displayed visual object is identical to a second attribute of a displayed visual object in a preset previous order. For example, when the attribute of the visual object is identical to the attribute of the visual object displayed in the second previous order, the device 100 may request, from the trainee, a first type of user input (e.g., the input of the left button of the input module 1200).

According to the inventive concept, the rule related to visual perceptual training may be a rule for requesting a second response from the trainee when the first attribute of the displayed visual object is different from the second attribute of the displayed visual object in the preset previous order. For example, when the attribute of the visual object is different from the attribute of the visual object displayed in the second previous order, the device 100 may request, from the trainee, a second type of user input (e.g., the input of the right button of the input module 1200).

It is noted that the type of response requested by the device 100 may be changed according to rules related to visual perceptual training, such as requesting the absence of a user input from the trainee, instead of requesting the first type of user input and the second type of user input from the trainee.

That is, according to the inventive concept, the device 100 may request a first response when the first pattern orientation of a displayed Gabor patch is identical to the second pattern orientation of a Gabor patch displayed in a preset previous order, and request a second response when the first pattern orientation of the displayed Gabor patch is different from the second pattern orientation of the Gabor patch displayed in the preset previous order.

Referring to FIG. 10, the device 100 may sequentially display Gabor patches having various pattern orientations as a visual object having a test value of a specific attribute (pattern orientation) in a training session according to the third example. Here, the device 100 may request a first response when the first pattern orientation of a displayed Gabor patch is identical to the second pattern orientation of a Gabor patch displayed in a second previous order, and request a second response when the first pattern orientation of the displayed Gabor patch is different from the second pattern orientation of the Gabor patch displayed in the second previous order.

The device 100 may request the trainee to respond to a rule related to visual perceptual training. For example, the device 100 may request a response from the trainee in a training session, the response corresponding to "order 3: second response, order 4: second response, order 5: first response, order 6: second response."

The device 100 may check the trainee's response in the training session. For example, the device 100 may receive and check a response from the trainee, the response including "order 3: second response, order 4: second response, order 5: second response, order 6: second response."

The device 100 may determine whether the checked response is correct. For example, the device 100 may determine whether a checked response is correct according to a rule based on the displayed visual object, a visual object displayed in the N-th previous order, and the type of the checked response. Referring to FIG. 10, the device 100 may request the second response from the trainee because the pattern orientation of a displayed Gabor patch in order 3 is different from the pattern orientation of a displayed Gabor patch displayed in order 1, and when the checked response is the second response, determine that the checked response is correct. Also, the device 100 may request the first response from the trainee because the pattern orientation of a displayed Gabor patch displayed in order 5 is identical to the pattern orientation of a displayed Gabor patch displayed in order 3, and when the checked response is the second response, determine that the checked response is incorrect.

That is, the device 100 may determine whether the checked response is correct or incorrect, such as "order 3: correct, order 4: correct, order 5: incorrect, order 6: correct" in the training session.

In addition, the device 100 may display various Gabor patches, such as Gabor patches having a pattern orientation other than Gabor patches having horizontal or vertical stripes, such as Gabor patches displayed in order 6 of FIG. 10.

According to the inventive concept, the device 100 may change the difficulty in the training session. For example, the controller 1500 may increase a preset size of a previous order N to increase the difficulty of the training session.

It is noted that the training session according to the embodiment may be provided using other perceptual stimuli without being not limited to the above description.

The hippocampus also plays a very important role in human spatial perception. Specifically, the hippocampus remembers spatiotemporal information received from sensory organs, and is also involved in egocentric and/or allocentric processing of the spatiotemporal information. Therefore, even when navigation training related to spatial perception processing is provided, the hippocampus is similarly stimulated, so that the cognitive ability of the trainee may be improved.

According to the inventive concept, the device 100 may further stimulate the hippocampus by providing a training session for improving cognitive ability in which perception training and navigation training are performed together, thereby further improving the cognitive ability of the trainee.

For example, the device 100 may provide the training session according to the first to third examples described above on a background image for navigation. Specifically, the training session according to the first to third examples may be provided in the background image including a virtual vehicle and a virtual road for navigation.

Further, each response of the training session according to the first to third examples may be related to movement of a vehicle in a specific orientation.

In addition, the training session according to the first to third examples may request an additional response related to the movement of the vehicle. Here, the background image may include an obstacle that prevents movement of the vehicle, and the additional response may be related to steering the vehicle such that the vehicle does not collide with the obstacle.

Figure 11:
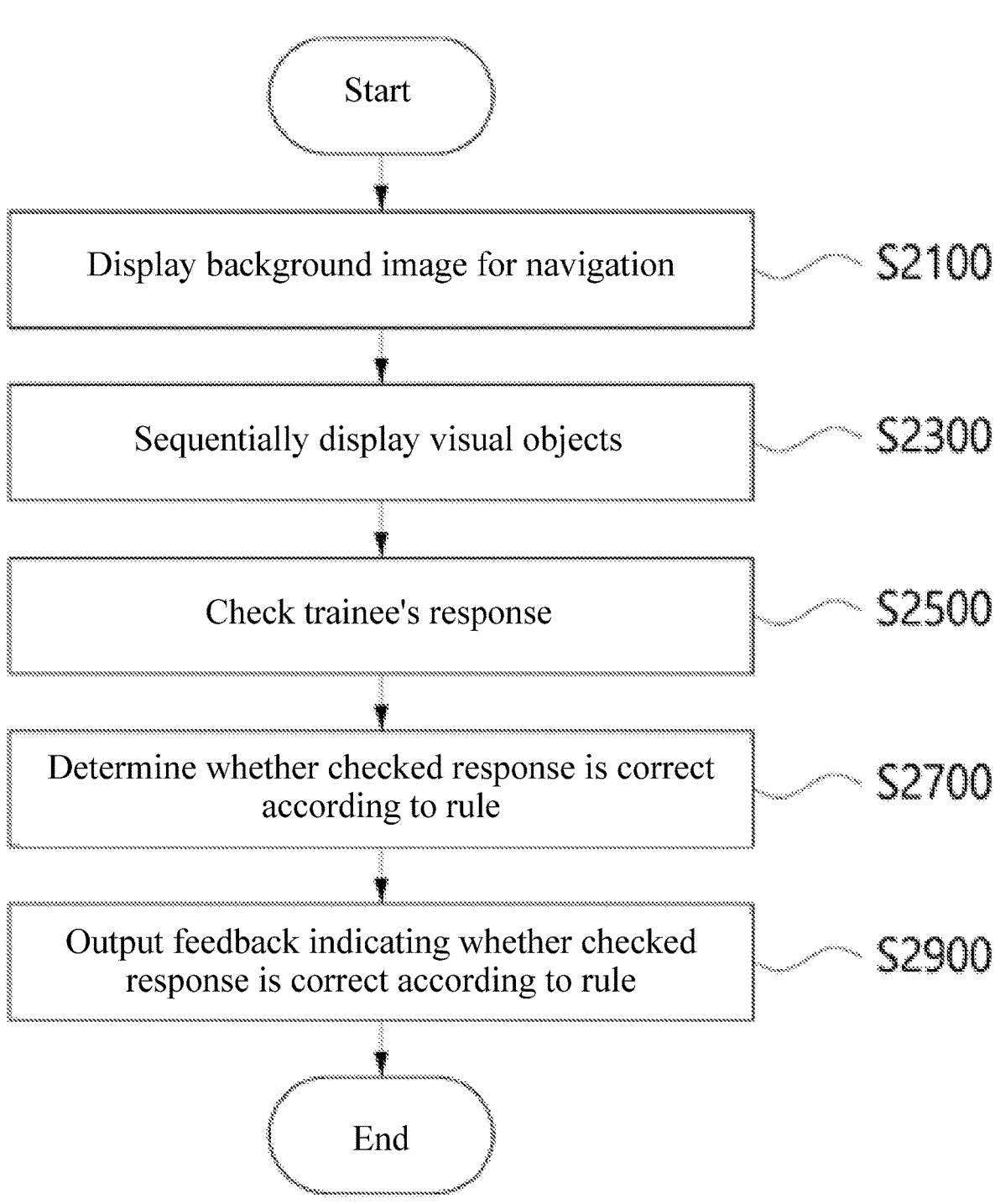
FIG. 11 is a flowchart of a method for providing a navigation training session according to the inventive concept.

FIG. 11 is a flowchart of a method for providing a navigation training session according to the inventive concept.

Referring to FIG. 11, a method for providing a navigation training session according to the inventive concept may include displaying a background image for navigation (S2100), sequentially displaying visual objects (S2300), checking a trainee's response related to the displayed visual object (S2500), determining whether the checked response is correct according to a rule (S2700), and outputting a feedback indicating whether the checked response is correct (S2900).

According to the inventive concept, the device 100 may display an image for navigation (S2100).

Figure 12:
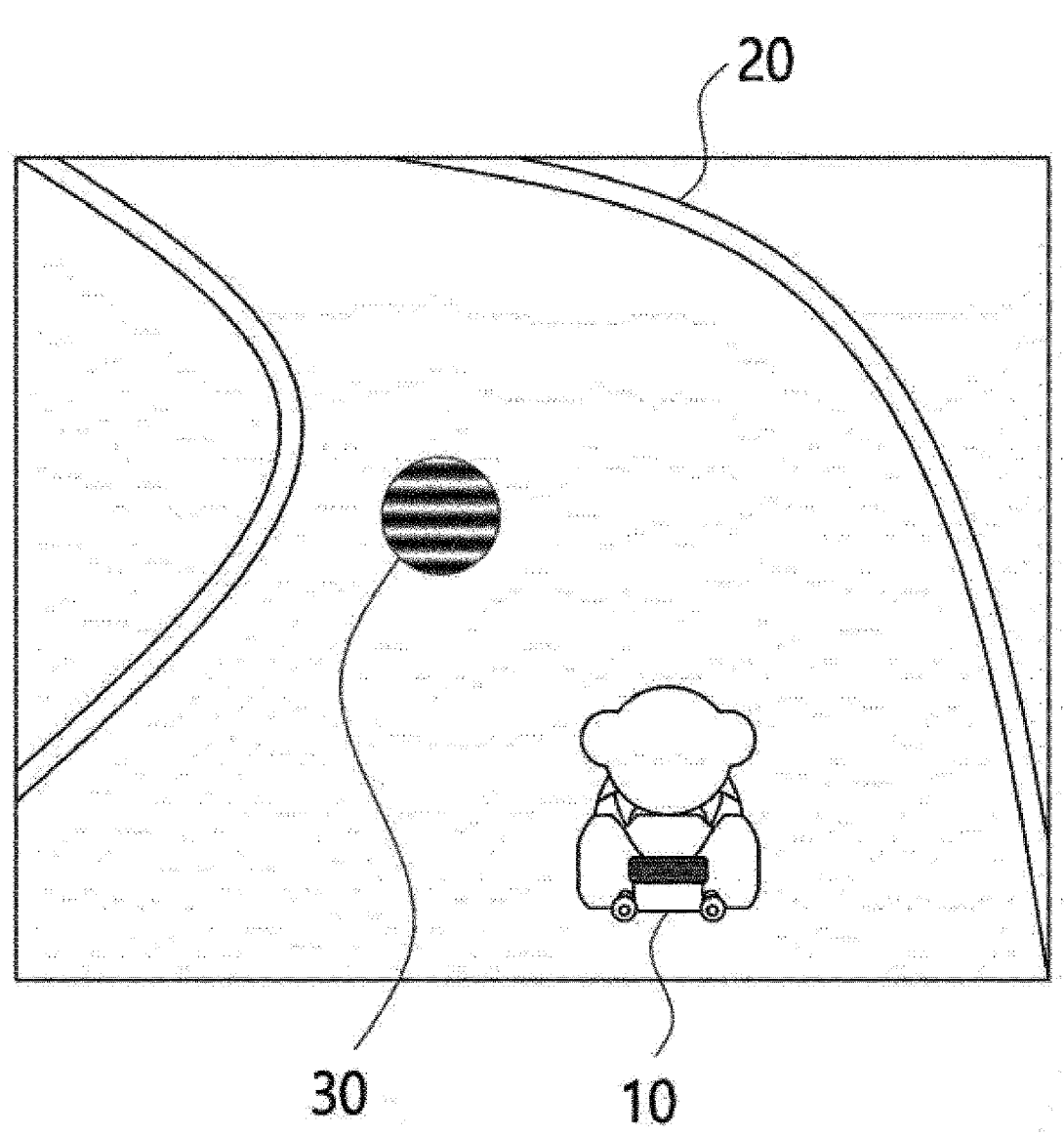
FIGS. 12 to 14 are diagrams regarding background images of a navigation training session for visual perceptual training according to the inventive concept.
Figure 13:
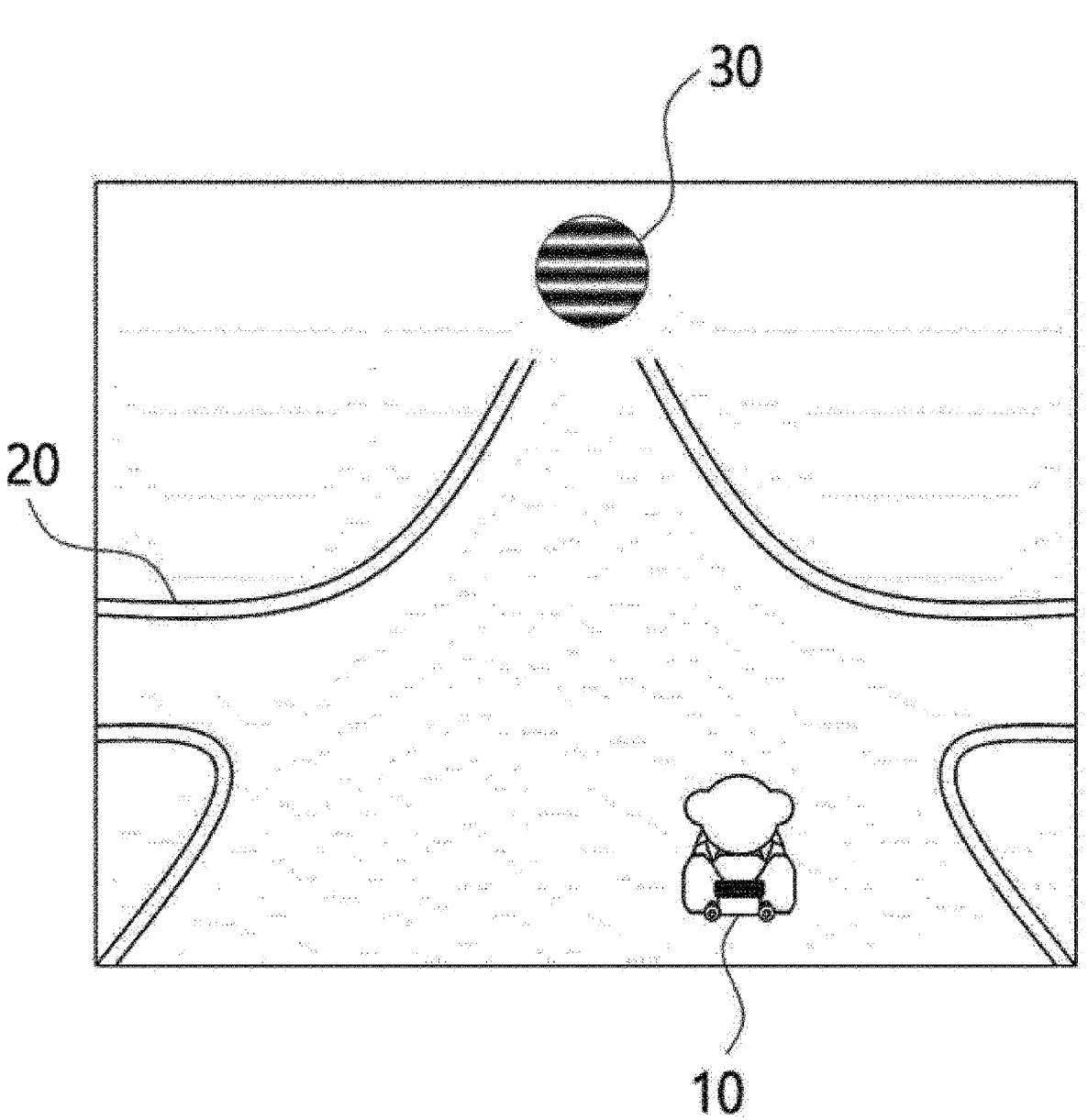
Figure 14:
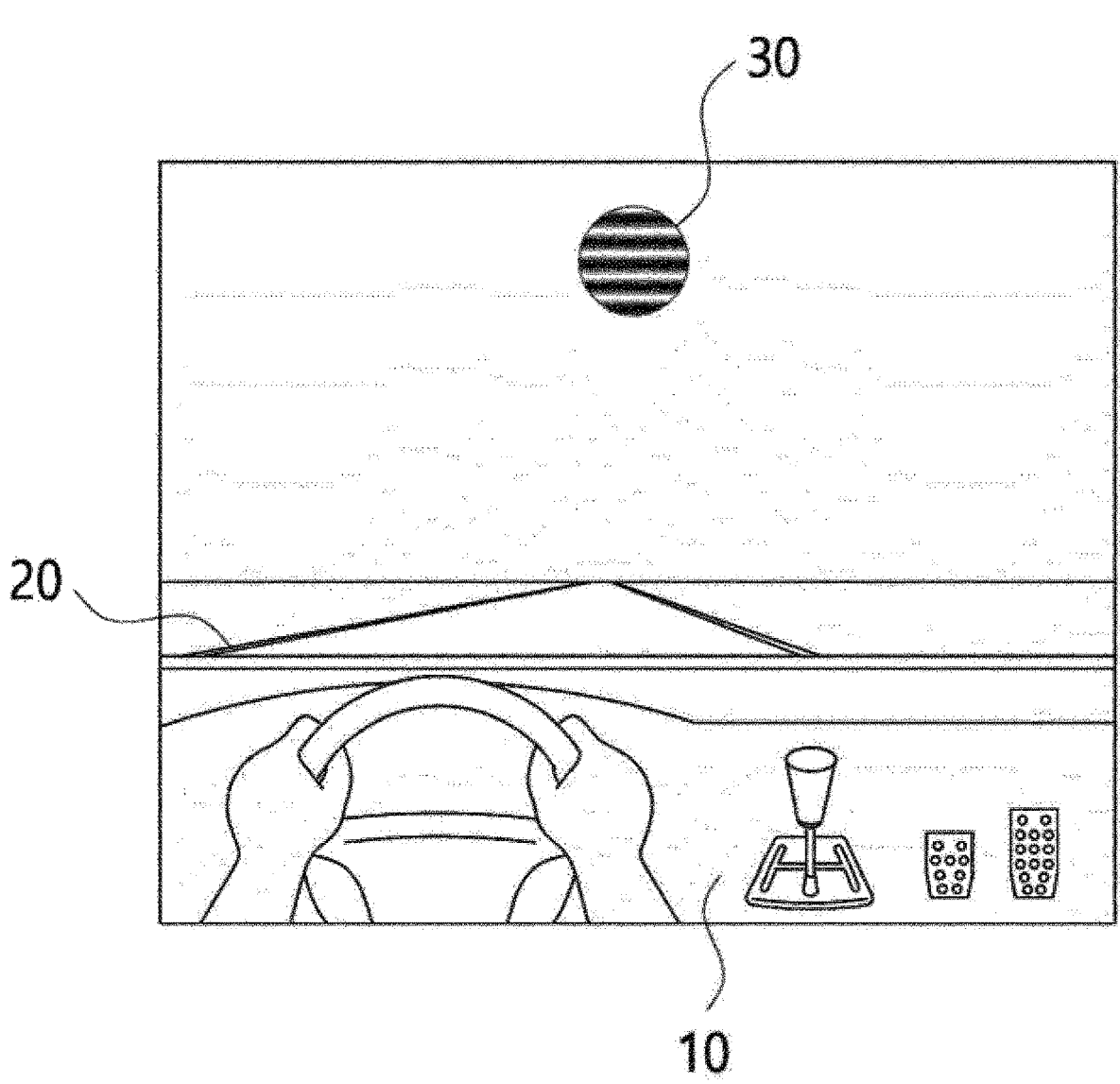

FIGS. 12 to 14 are diagrams showing background images of a navigation training session for visual perceptual training according to the inventive concept.

Referring to FIGS. 12 to 14, the device 100 may display a background image including a virtual road 20 and a virtual vehicle 10.

Referring to FIG. 12, the device 100 may display the background image for navigation in a third person perspective.

The device 100 may display the virtual road 20 and the virtual vehicle 10 in a third person perspective, and receive an input of a trainee related to the movement of the vehicle 10 from the input module 1200.

For example, the controller 1500 may receive the trainee's response corresponding to the movement of the vehicle 10 in a specific orientation from the input module 1200. Specifically, the controller 1500 may receive, from the input module 1200, an input of a trainee who controls the vehicle 10 to avoid collision with an obstacle placed on the road 20. Also, the controller 1500 may receive, from the input module 1200, an input of a trainee who controls the vehicle 10 not to deviate to the outside of the road 20.

Referring to FIG. 13, the device 100 may display a background image including a forked road.

The device 100 may display the forked road, and receive an input of a trainee related to the movement of the vehicle 10 from the input module 1200.

For example, the controller 1500 may receive the trainee's response corresponding to the movement of the vehicle 10 in a specific orientation from the input module 1200. Specifically, the controller 1500 may receive, from the input module 1200, an input of a trainee who controls the vehicle 10 to enter a road in a specific orientation in the forked road.

Referring to FIG. 14, the device 100 may display the background image for navigation in a first person perspective.

The device 100 may display the virtual road 20 and the virtual vehicle 10 in a first person perspective. For example, the controller 1500 may display the virtual road 20 and the vehicle 10 which drives on the virtual road 20 through the output module 1100, the vehicle 10 including a steering wheel, a gear lever, a pedal, and the like.

It is noted that the background image for navigation is not limited to the above described image, and may include additional elements such as an obstacle that prevents movement of the vehicle, an avatar riding in the vehicle, another vehicle, and a traffic light.

According to the inventive concept, the device 100 may sequentially display visual objects to provide an identification task to a trainee in a navigation training session (S2300).

For example, the controller 1500 may display a visual object for visual perceptual training through the output module 1100. Here, the controller 1500 may request a response related to the visual object from the trainee.

The trainee's response may be related to the movement of the vehicle. For example, a first response of the trainee with respect to the visual object may correspond to movement of the vehicle in a first orientation, and a second response of the trainee with respect to the visual object may correspond to movement of the vehicle in a second orientation.

Referring to FIGS. 12 to 14, the device 100 may display a Gabor patch 30 for visual perceptual training at a specific location.

According to the inventive concept, the device 100 may check the type of the trainee's response related to the visual object displayed in the navigation training session (S2500).

The controller 1500 may receive an input of the trainee related to the visual object from the input module 1200. For example, the controller 1500 may receive the input of the trainee related to the identification of the visual object as an identification task from the input module 1200.

Also, the controller 1500 may check what type of response the obtained response is. Here, each of types of responses may correspond to each displayed visual object. For example, the controller 1500 may request, from the user, a response with a first type (for example, input of a left button of the input module 1200) when a first visual object is displayed, and request, from the user, a response with a second type (for example, input of a right button of the input module 1200) when a second visual object is displayed. It is noted that each type of responses may correspond to an attribute of each displayed visual object. Also, the types of responses include various types of user inputs, and the absence of a user input may be one of the types of response.

The checked type of the response of the trainee may be related to the movement of the vehicle. For example, each response may be related to movement of the vehicle in a specific orientation. It is noted that each response is not related to the movement of the vehicle, and the device 100 may receive an additional response related to the movement of the vehicle.

According to the inventive concept, the device 100 may determine whether the checked response in the navigation training session is correct according to the rule (S2700).

The controller 1500 may determine whether the checked response is correct according to the rule based on the displayed visual object and the type of the checked response.

Specifically, the controller 1500 may compare the type of a response corresponding to the displayed visual object with the checked response, and when the two responses are the same, determine that the response is correct. For example, when the first visual object is displayed, if the checked response is the first response corresponding to the first visual object, the controller 1500 may determine that the trainee has input a correct response.

According to the inventive concept, the device 100 may output a feedback indicating whether a response checked in the navigation training session is correct (S2900).

The controller 1500 may output the feedback indicating whether the checked response is correct through the output module 1100. For example, the controller 1500 may display a message, a video, an image, or the like regarding whether the checked response is correct, through the output module 1100.

As another example, the controller 1500 may audibly output a voice, a melody, an alarm, or the like regarding whether the checked response is correct, through the output module 1100. As another example, the controller 1500 may tactfully output various types of vibrations regarding whether the checked response is correct through the output module 1100.

Also, the controller 1500 may output a feedback indicating whether the navigation of the vehicle is accurate through the output module 1100 and/or the output module 1100. For example, the controller 1500 may output a feedback indi-cating that the driving of the vehicle is not properly per-formed when the vehicle deviates from a road or collides with an obstacle through the output module 1100.

Hereinafter, various embodiments of a navigation training session provided by the device 100 will be described.

Fourth Example

Hereinafter, a training session according to a fourth example provided by the device 100 will be described.

In the training session according to the fourth example, the device 100 may sequentially display visual objects on a background image including a virtual road and a virtual vehicle, and request a response related to the visual object from a trainee.

The rule related to the visual perceptual training applied in the fourth example of the training session for the visual perceptual training may be the rule in the third example. The rule related to the visual perceptual training according to the fourth example is to provide a trainee with an identification task and a cognitive task together in the training session, wherein the trainee needs to identify a displayed visual object, remember a visual object displayed in a previous specific order, and input a correct response. That is, the rule related to visual perceptual training may be a rule for comparing the displayed visual object with a visual object displayed in a preset previous order and requesting a correct response from the trainee.

The rule related to visual perceptual training may be a rule for requesting a first response from the trainee when a first attribute of a displayed visual object is identical to a second attribute of a displayed visual object in a preset previous order. For example, when the attribute of the visual object is identical to the attribute of the visual object displayed in the second previous order, the device 100 may request, from the trainee, a first type of user input (e.g., the input of the left button of the input module 1200).

The rule related to visual perceptual training may be a rule for requesting a second response from the trainee when a first attribute of a displayed visual object is different from a second attribute of a displayed visual object in a preset previous order. For example, when the attribute of the visual object is different from the attribute of the visual object displayed in the second previous order, the device 100 may request, from the trainee, a second type of user input (e.g., the input of the right button of the input module 1200). It is noted that the type of response requested by the device 100 may be changed according to rules related to visual percep-tual training, such as requesting the absence of a user input from the trainee, instead of requesting the first type of user input and the second type of user input from the trainee.

According to the inventive concept, the trainee's response with respect to the displayed visual object may be related to the movement of the vehicle. For example, the type of trainee's response with respect to the visual object may be related to determination of whether the vehicle is to pass or avoid the visual object. Specifically, the first response may correspond to the vehicle passing the visual object, and the second response may correspond to the vehicle avoiding the visual object. It is noted that the trainee's response related to the visual object is independent of the movement of the vehicle, and an additional response of the trainee related to the movement of the vehicle may be received.

FIGS. 15A to 15D are diagrams regarding a fourth example of a training session of the inventive concept.

Referring to FIGS. 15A to 15D, the device 100 may sequentially display Gabor patches 31, 32, 33, and 34 having various pattern orientations as an object with a specific attribute (e.g., pattern orientation) in a background image including the virtual road 20 and the virtual vehicle 10.

The device 100 may request a first response when the first pattern orientation of a displayed Gabor patch is identical to the second pattern orientation of a Gabor patch displayed in a second previous order, and request a second response when the first pattern orientation of the displayed Gabor patch is different from the second pattern orientation of the Gabor patch displayed in the second previous order.

Here, the first response may correspond to the vehicle 10 passing through the displayed Gabor patches 31, 32, 33, and 34, and the second response may correspond to the vehicle 10 avoiding the displayed Gabor patches 31, 32, 33, and 34.

Also, the device 100 may check the trainee's response in the training session. For example, the device 100 may check the types of the trainee's responses related to the Gabor patches 31, 32, 33, and 34 sequentially displayed.

Also, the device 100 may determine whether a checked response is correct according to a rule based on the displayed visual object, a visual object displayed in the N-th previous order, and the type of the checked response. Here, N is a positive integer.

Figures 15A, 15B, 15C, 15D:
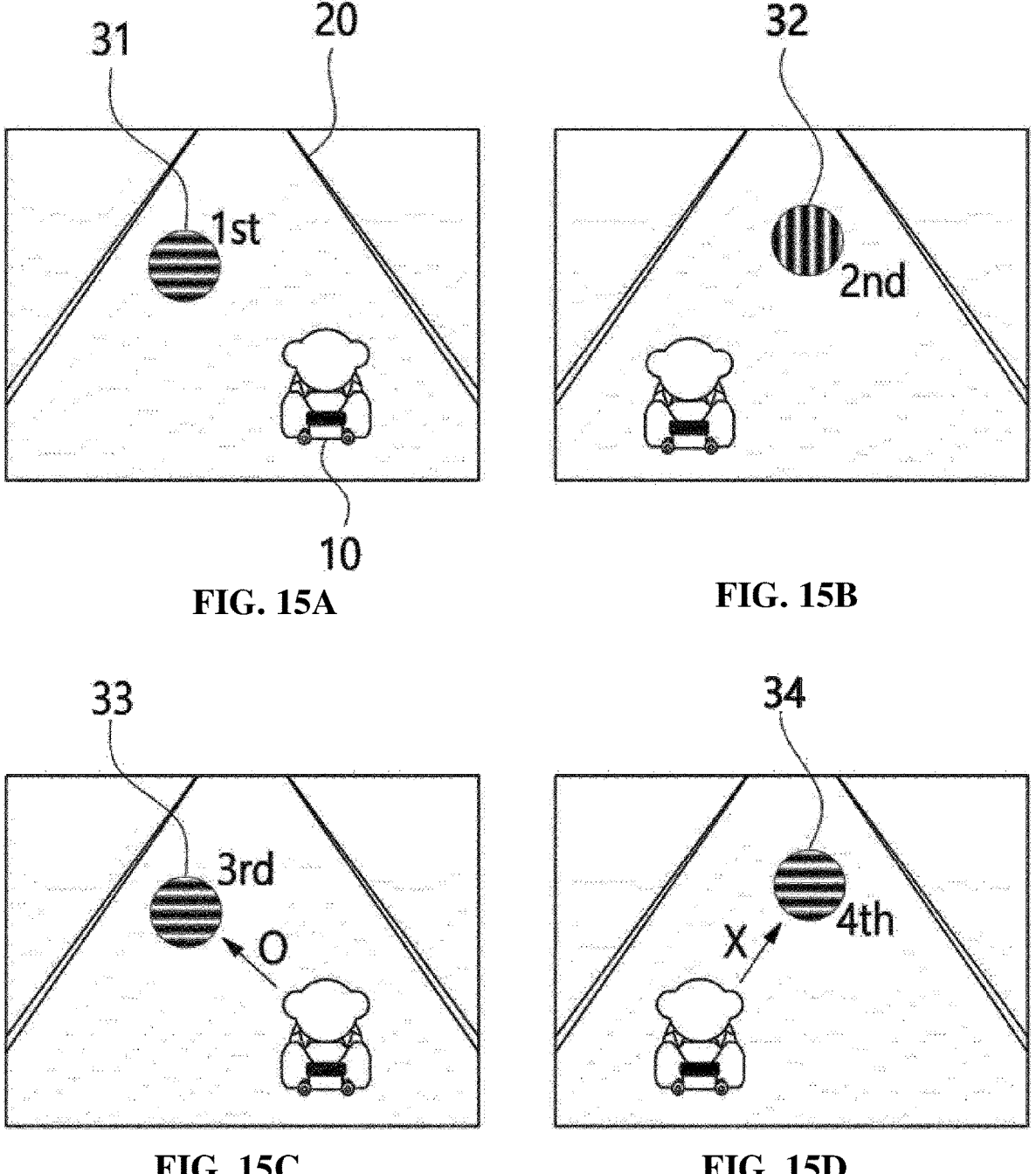
FIGS. 15A to 15D are diagrams regarding a fourth example of a training session of the inventive concept.

Referring to FIG. 15C, the device 100 may determine that a first type of user input corresponding to the passage of the Gabor patch 33 of the vehicle 10 is a correct response because the Gabor patch 33 displayed is a Gabor patch having a horizontal pattern orientation, and the Gabor patch 31 displayed first is also a Gabor patch having a horizontal pattern orientation.

Referring to FIG. 15D, the device 100 may determine that a second type of user input corresponding to the avoidance of the Gabor patch of the vehicle 10 is a correct response because the Gabor patch 34 displayed fourth is a Gabor patch having a horizontal pattern orientation, and the Gabor patch 32 displayed second is a Gabor patch having a vertical pattern orientation.

Of course, the device 100 may display a Gabor patch having various attributes, such as a Gabor patch having a pattern orientation other than the Gabor patch having a horizontal or vertical pattern orientation.

According to the inventive concept, the device 100 may change the difficulty of visual perceptual training in the training session. For example, the controller 1500 may change visual objects to be displayed to increase or decrease the difficulty of visual perceptual training in the training session.

It is noted that the training session according to the embodiment may be provided using other perceptual stimuli without being not limited to the above description.

Fifth Example

Hereinafter, a training session according to a fifth example provided by the device 100 will be described.

In the training session according to the fifth example, the device 100 may sequentially display a test object with the test value of a specific attribute on a background image including a virtual road and a virtual vehicle, and request a response related to the test value from a trainee.

The rule related to the visual perceptual training which is applicable to a training session according to the fifth example is to provide an identification task to a trainee, wherein the trainee needs to identify a test object having the test value of a displayed specific attribute, compare the test object with a reference object having a reference value of the specific attribute, and input a correct response. That is, the rule related to visual perceptual training may be a rule for requesting the type of a specific response from a trainee when the displayed test object is identical to a preset reference object, and requesting the type of a different response from the trainee when the displayed test object is different from the preset reference object.

The rule may be a rule for requesting a first response from the trainee when the displayed test object is identical to a reference object. Specifically, the rule may be a rule requesting the first response from the trainee when the test value of the specific attribute of the displayed test object is identical to the reference value of the specific attribute of the reference object. For example, when the reference object is a Gabor patch having a horizontal pattern orientation and a displayed test object is a Gabor patch having a horizontal pattern orientation, the device 100 may request a first type of user input (e.g., the input of the left button of the input module 1200) from the trainee.

Also, the rule may be a rule for requesting a second response from the trainee when the displayed test object is different from the second reference object. Specifically, the rule may be a rule requesting a second response from the trainee when the test value of the specific attribute of the displayed test object is different from the reference value of the specific attribute of the reference object. For example, when the reference object is a Gabor patch having a vertical pattern orientation and a displayed test object is a Gabor patch having a horizontal pattern orientation, the device 100 may request a second type of user input (e.g., the absence of a user input) from the trainee.

It is noted that the type of response requested by the device 100 may be changed according to rules related to visual perceptual training, such as requesting a second type of user input, instead of requesting the absence of user input from the trainee.

According to the inventive concept, the trainee's response with respect to the displayed visual object may not be related to the movement of the vehicle. For example, the device 100 may request an additional response related to movement of the vehicle from the trainee. Here, the device 100 may display an obstacle that prevents the movement of a vehicle on a road and request an additional response from a trainee who controls the vehicle such that the vehicle does not collide with the obstacle. Through this, the device 100 may request a multi-cognitive load from the trainee by providing both navigation training and visual perceptual training. It is noted that the trainee's response with respect to the visual object is related to the movement of the vehicle, and the movement of the vehicle may be controlled according to the type of each response.

Also, the device 100 may change the difficulty of the training session. For example, the controller 1500 may increase the difficulty of visual perceptual training in the training session by decreasing a difference between a reference object and a test object in displaying the reference object and the test object different from the reference object. Specifically, when the controller 1500 displays the second test object having the attribute of a test value that is different from the reference value of a specific attribute of the reference object, the controller 1500 may change the difficulty by adjusting an average difference between the reference value and the test value of the second test object. Here, the average difference may be smaller as the difficulty level is higher. Through this, the device 100 may request the trainee to more accurately memorize the reference object, thereby improving the trainee's cognitive ability.

Also, the device 100 may change a specific attribute of a reference object and a test object. For example, when the vehicle passes through a finish line, the controller 1500 may change the specific attribute of the reference object and the test object from pattern orientation to pattern contrast. For example, the controller 1500 may change the specific attribute of the reference object and the test object from pattern orientation to pattern contrast after a preset period has elapsed.

FIGS. 16A to 16D are diagrams showing a fifth example of a training session of the inventive concept.

FIGS. 16A to 16D, the device 100 may display a Gabor patch having stripes in various orientations as a visual object with a specific attribute (for example, pattern orientation) on a background image including the virtual road 20, the virtual vehicle 10, and an obstacle 60 that prevents the movement of the vehicle. The reference objects 40, 41, 42, and 43 provided as Gabor patches and the test objects 50, 51, 52, and 53 provided as Gabor patches may be displayed at different locations of the background image. Specifically, the reference objects 40, 41, 42, and 43 may be displayed in the upper right region, and the test objects 50, 51, 52, and 53 may be displayed on the helmet of an avatar riding in the vehicle 10.

The device 100 may request a first response from the trainee when the test value of the pattern orientation of the displayed test objects 50, 51, 52, and 53 is identical to the reference value of the pattern orientation of the reference objects 40, 41, 42, and 43, and request a second response from the trainee when the test value of the pattern orientation of the displayed test objects 50, 51, 52, and 53 is different from the reference value of the pattern orientation of the reference objects 40, 41, 42, and 43.

Also, the device 100 may check the trainee's response in the training session. For example, the device 100 may check the types of the trainee's responses with respect to the test objects 50, 51, 52, and 53 and the reference objects 40, 41, 42, and 43, which are sequentially displayed.

Also, the device 100 may determine whether a checked response is correct according to a rule based on the test value and the type of the checked response.

Figures 16A, 16B, 16C, 16D:
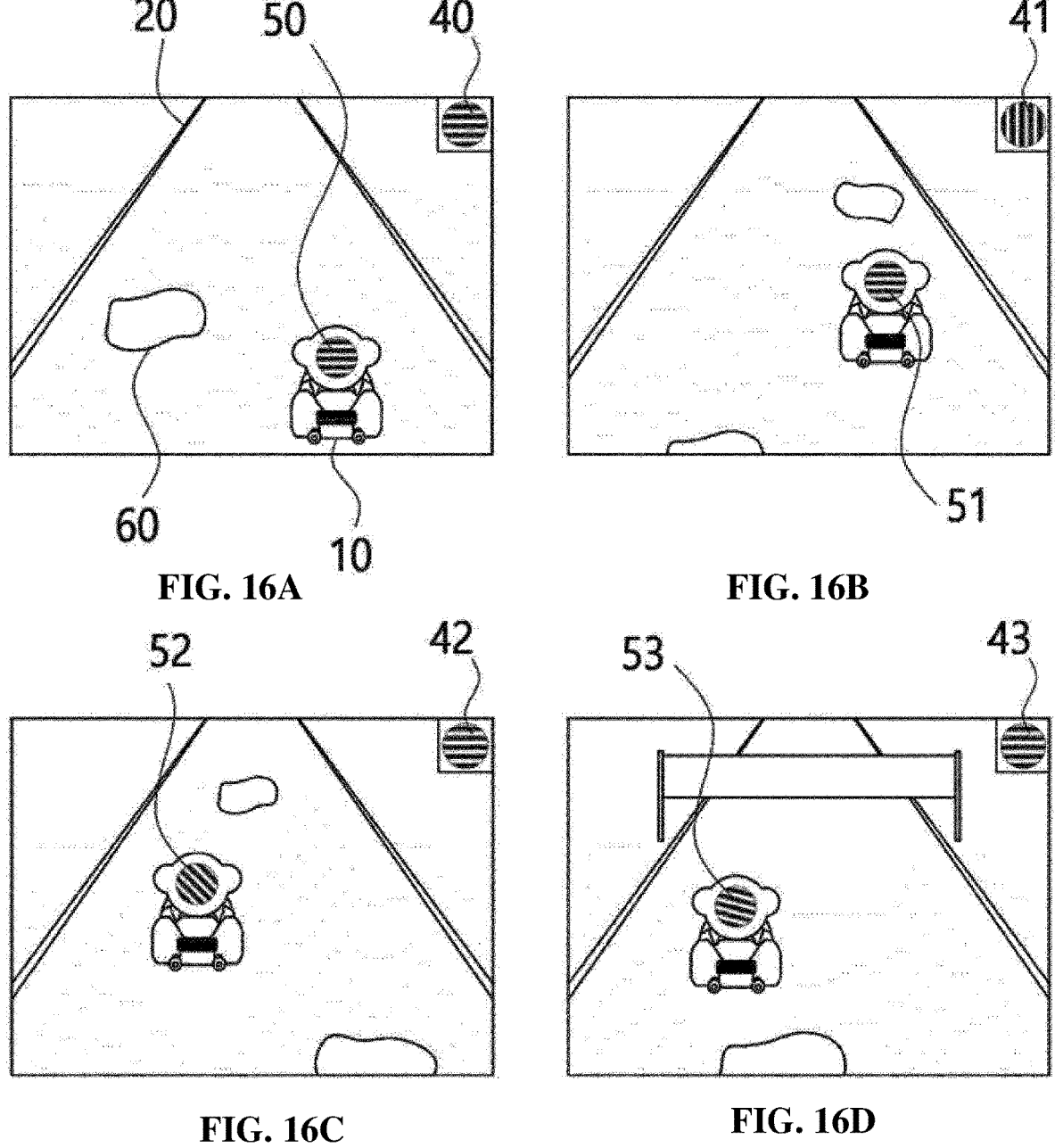
FIGS. 16A to 16D are diagrams regarding a fifth example of a training session of the inventive concept.

Referring to FIG. 16A, when the reference object 40 that is a Gabor patch having horizontal stripes and the test object 50 that is a Gabor patch having the same horizontal stripes as the reference object 40 are displayed, the device 100 may determine the first response as a correct response.

Referring to FIG. 16B, when the reference object 41 that is a Gabor patch having vertical stripes and the test object 51 that is a Gabor patch having the different horizontal stripes from the reference object 41 are displayed, the device 100 may determine the second response as a correct response.

Also, the device 100 may additionally obtain a user input for steering the vehicle such that the vehicle 10 does not collide with the obstacle 60 located on the road 20.

Referring to FIG. 16D, the device 100 may change an attribute of the reference object 43 and the test object 53 from pattern orientation to pattern contrast when the vehicle 10 passes through a finish line 70 that changes the specific attribute of the reference object 43 and the test object 53.

Referring to FIGS. 16C and 16D, it can be seen that the difference between the pattern orientation of the test object 53 and the pattern orientation of the reference object 42 is smaller than the difference between the pattern orientation of the test object 52 and the pattern orientation of the reference object 43, so that the difficulty of visual perceptual training of FIG. 16D is higher than that of FIG. 16C.

Sixth Example

Hereinafter, a training session according to a sixth example provided by the device 100 will be described.

In the training session according to the sixth example, the device 100 may output a perceptual stimulus indicating a moving orientation of the vehicle to a background image including a virtual road and a virtual vehicle, and request a response related to the perceptual stimulus from a trainee. Here, the virtual road may include a plurality of forked roads.

The rule related to the visual perceptual training applied in the training session according to the sixth example is to provide an identification task to the trainee in the training session, wherein the trainee needs to identify a displayed orientation indicator, and input a response to move a vehicle according to the identified orientation indicator.

The rule related to visual perceptual training may be a rule requesting a response corresponding to the displayed orientation indicator. For example, the rule related to visual perceptual training may be a rule requesting a first response corresponding to a first orientation indicator when the first orientation indicator is displayed, and requesting a second response corresponding to a second orientation indicator when the second orientation indicator is displayed. Here, the response may be related to the movement of the vehicle. For example, the first response may move the vehicle in a first orientation, and the second response may move the vehicle in a second orientation.

Also, the rule related to visual perceptual training may be a rule requesting a response corresponding to a specific attribute of a displayed orientation indicator. For example, the rule related to visual perceptual training may be a rule requesting a first response corresponding to a first orientation indicator with first attribute when the first orientation indicator with the first attribute is displayed, and requesting a second response corresponding to a second orientation indicator with first attribute when the second orientation indicator with the second attribute is displayed. Here, the response may be related to the movement of the vehicle. For example, the first response may move the vehicle in a first orientation, and the second response may move the vehicle in a second orientation.

It is noted that the type of response requested by the device 100 may be changed according to rules related to visual perceptual training, such as requesting the absence of a user input from the trainee, instead of requesting the specific type of user input from the trainee.

The device 100 may check the trainee's response related to a displayed orientation indicator. Here, the trainee's response may be related to the movement of the vehicle. For example, the first response may move the vehicle in a first orientation, and the second response may move the vehicle in a second orientation.

Also, the device 100 may determine whether a checked response is correct according to a rule based on the orientation indicator and the type of the checked response. For example, the controller 1500 may determine the first response corresponding to the first orientation indicator as a correct response. Also, the controller 1500 may determine the second response corresponding to the second orientation indicator as a correct response.

Also, the device 100 may change the difficulty of the training session. For example, the controller 1500 may increase the difficulty of the training session by increasing the number of types of orientation indicators.

According to an embodiment, the device 100 may provide a navigation training session using different perceptual stimuli.

The device 100 may provide an orientation indicator through another perceptual stimulus. For example, the device 100 may output an auditory stimulus serving as an orientation indicator together with a background image including a virtual road and a virtual vehicle for auditory perceptual learning. Here, the other perceptual stimuli may include auditory stimuli, tactile stimuli, gustatory stimuli, olfactory stimuli, and the like. In addition, the perceptual stimuli may have specific attributes. For example, the auditory stimulus may have attributes such as intensity, speed, pitch, rhythm, and length.

A rule related to perceptual training may be a rule requesting a response corresponding to an output orientation indicator. For example, the rule related to auditory perceptual training may be a rule requesting a first response corresponding to a first orientation indicator when the first orientation indicator is audibly output and requesting a second response corresponding to a second orientation indicator when the second orientation indicator is audibly output. Here, the response may be related to the movement of the vehicle. For example, the first response may move the vehicle in a first orientation, and the second response may move the vehicle in a second orientation.

Figure 17:
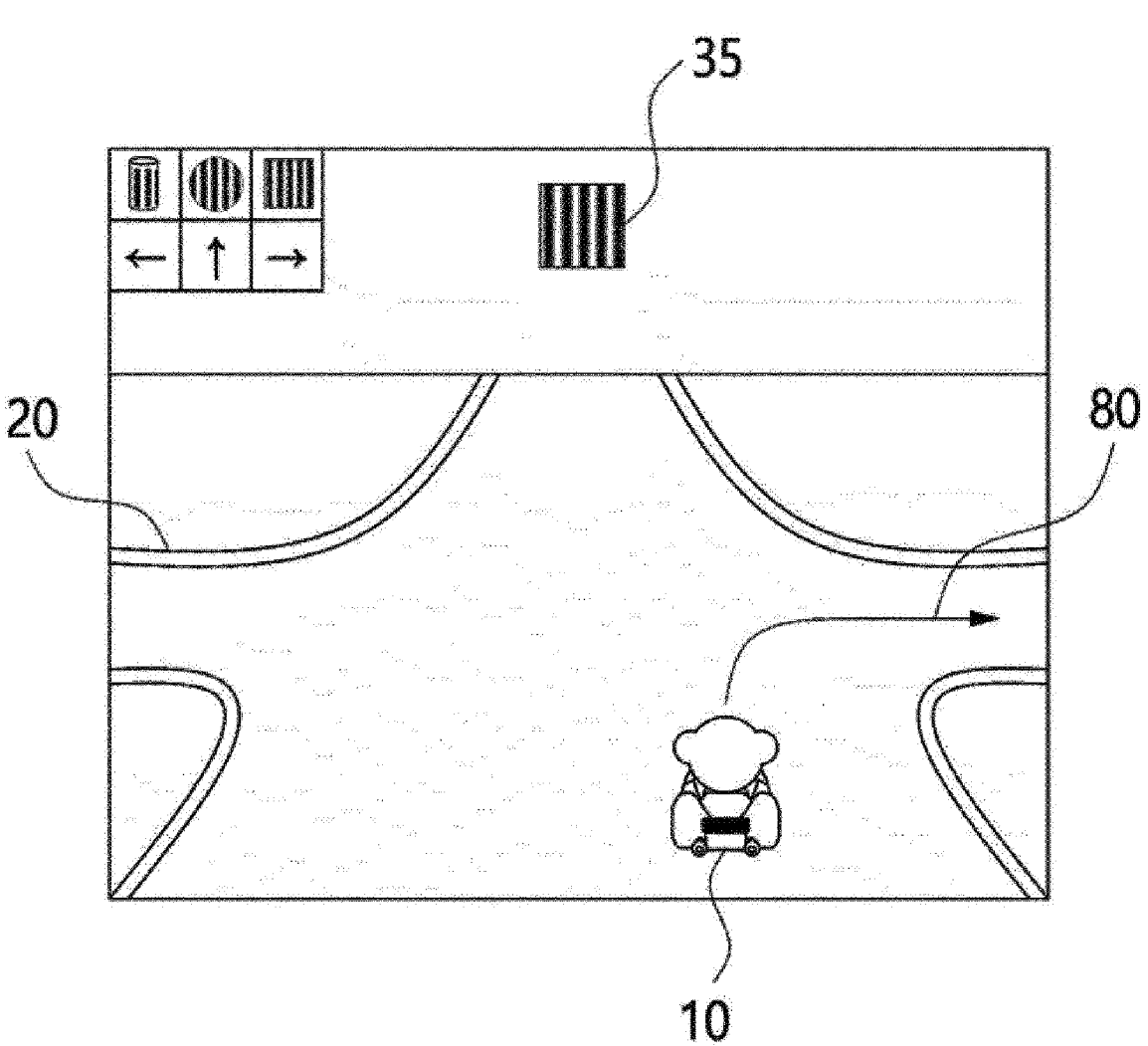
FIG. 17 is a diagram regarding sixth example of a training session of the inventive concept.

FIG. 17 is a diagram showing a sixth example of a training session of the inventive concept.

Referring to FIG. 17, the device 100 may display various shapes of Gabor patches as an orientation indicator on a background image including the virtual road 20 including a plurality of forked roads and the virtual vehicle 10. Here, a cylindrical Gabor patch indicates movement to the left, a circular Gabor patch indicates forward movement, and a rectangular Gabor patch indicates movement to the right.

The device 100 may request a response corresponding to the displayed orientation indicator 35 from the trainee. For example, the device 100 may display a first response corresponding to the cylindrical Gabor patch when the cylindrical Gabor patch is displayed, a second response corresponding to the circular Gabor patch when the circular Gabor patch is displayed, and a third response corresponding to the rectangular Gabor patch when the rectangular Gabor patch is displayed. Here, the first response may correspond to the movement of the vehicle 10 to the left, the second response may correspond to the forward movement of the vehicle 10, and the third response may correspond to the movement of the vehicle 10 to the right.

Also, the device 100 may check the trainee's response in the training session. For example, the device 100 may check the type of the trainee's response related to the displayed orientation indicator 35.

Also, the device 100 may determine whether a checked response is correct according to a rule based on the orientation indicator 35 and the type of the checked response.

Referring to FIG. 17, when the orientation indicator 35 that is a rectangular Gabor patch is displayed, the device 100 may determine a third reaction corresponding to the rectangular Gabor patch as a correct response. Here, the third reaction corresponds to the movement 80 to the right of the vehicle 10 so that the device 100 moves the vehicle 10 to the right road.

It is noted that the training session according to the embodiment may be provided using other perceptual stimuli without being not limited to the above description.

Seventh Example

Hereinafter, a training session according to a seventh example provided by the device 100 will be described.

In the training session according to the seventh example, the device 100 may display an orientation indicator with a specific pattern orientation on a background image including a virtual road and a virtual vehicle, and request a response related to the pattern orientation from a trainee.

The rule related to the visual perceptual training applied in the training session according to the seventh example is to provide an identification task, and the trainee identifies a visual object having a specific pattern orientation, and responds correctly according to the pattern orientation of the identified visual object.

The rule related to visual perceptual training may be a rule requesting a response corresponding to an orientation indicator having a displayed specific pattern orientation. Specifically, the rule related to visual perceptual training may be a rule requesting a response of moving the vehicle in the same movement orientation as the pattern orientation of the orientation indicator having a displayed specific pattern orientation.

For example, when the orientation indicator having the first pattern orientation is displayed, the device 100 may request a first reaction of moving the vehicle in the same first movement orientation as the first pattern orientation. Also, when the orientation indicator having the second pattern orientation is displayed, the device 100 may request a second reaction of moving the vehicle in the same second movement orientation as the second pattern orientation.

It is noted that the type of response requested by the device 100 may be changed according to rules related to visual perceptual training, such as requesting the absence of a user input from the trainee, instead of requesting the specific type of user input from the trainee.

The device 100 may check the trainee's response related to a displayed orientation indicator. The device 100 may check the trainee's response related to a displayed orientation indicator. Here, the trainee's response may be related to the movement of the vehicle.

Also, the device 100 may determine whether a checked response is correct according to a rule based on the orientation indicator and the type of the checked response. For example, the controller 1500 may determine the first reaction of moving the vehicle in the same first movement orientation as the first pattern orientation of the orientation indicator as the correct reaction. Also, the controller 1500 may determine the second reaction of moving the vehicle in the same second movement orientation as the second pattern orientation of the orientation indicator as the correct reaction.

Also, the device 100 may change the difficulty of the training session. For example, the controller 1500 may increase the number of forks to increase the difficulty of the training session.

Figure 18:
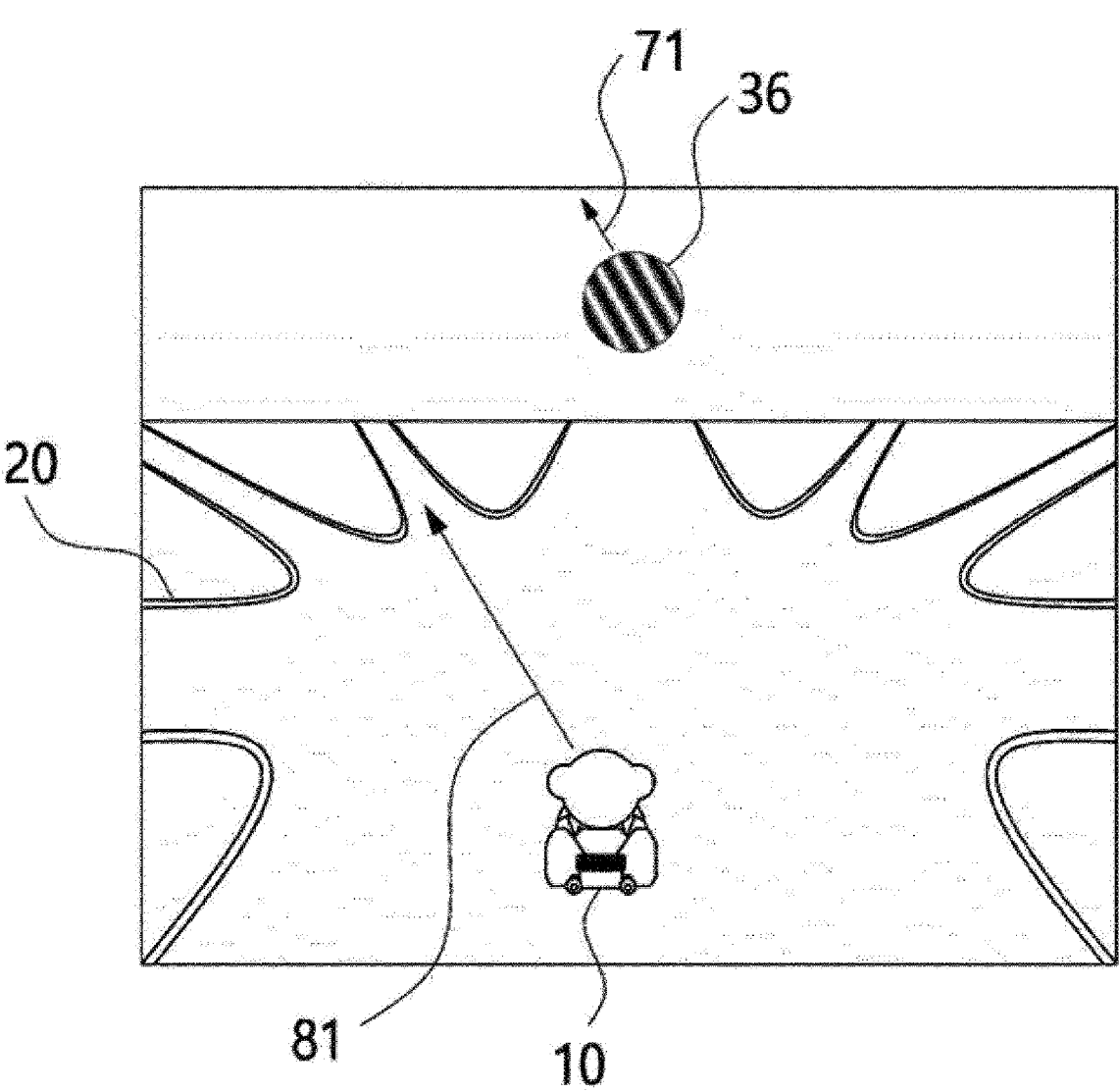
FIG. 18 is a diagram regarding a seventh example of a training session of the inventive concept.

FIG. 18 is a diagram regarding a seventh example of a training session of the inventive concept.

Referring to FIG. 18, the device 100 may sequentially display a Gabor patch having stripes in various orientations as an orientation indicator 36 having a pattern orientation 71 in a background image including the virtual road 20 and the virtual vehicle 10. Here, the virtual road may include a plurality of forked roads.

The device 100 may request the trainee's response to move the vehicle 10 in the same orientation as the pattern orientation 71 of the displayed orientation indicator 36.

Also, the device 100 may check the trainee's response in the training session. For example, the device 100 may check the type of the trainee's response related to the pattern orientation 71 of the displayed orientation indicator 36.

Also, the device 100 may determine whether a checked response is correct according to a rule based on the pattern orientation 71 and the type of the checked response.

Referring to FIG. 18, the device 100 may determine, as a correct response, a response to move the vehicle 10 in the same moving orientation 81 as the pattern orientation 71 when the orientation indicator 36 having the pattern orientation 71 is displayed. That is, the trainee needs to input a user input for moving the vehicle 10 into a road in the same orientation 81 as the specific pattern orientation 71.

Eighth Example

Hereinafter, a training session according to an eighth example provided by the device 100 will be described.

Figure 19:
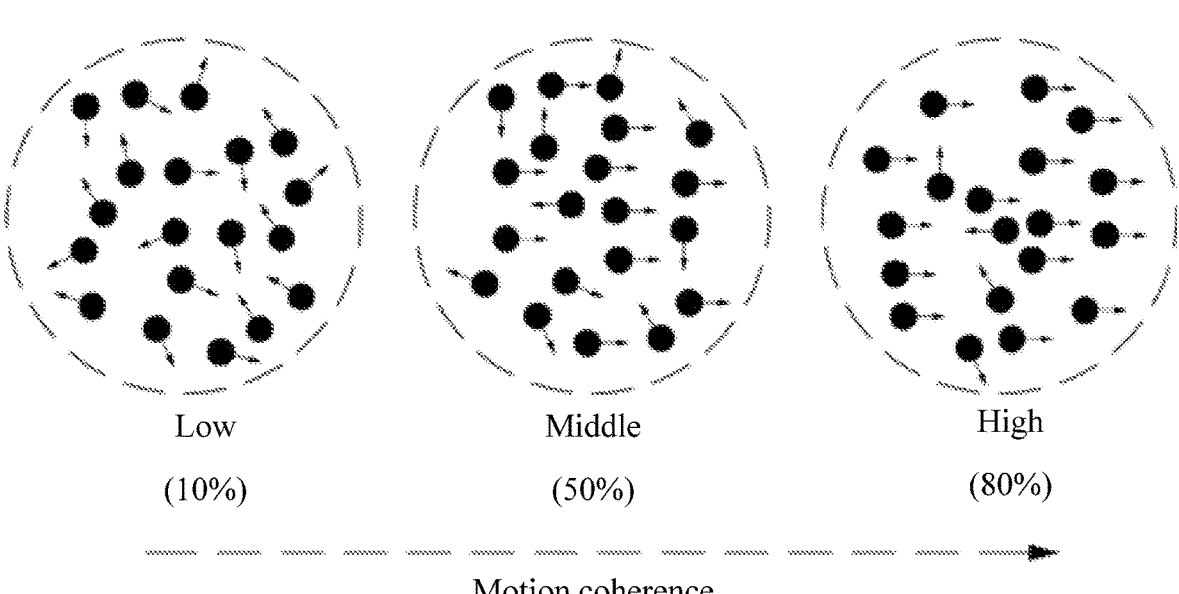
FIG. 19 is a diagram related to a direction indicator used in an eighth example of a training session of the inventive concept.

FIG. 19 is a diagram related to an orientation indicator used in an eighth example of a training session of the inventive concept.

Referring to FIG. 19, the orientation indicator may include a plurality of visual objects each moving in an individual orientation.

The orientation indicator may include visual objects that randomly move and visual objects that move coherently in a specific orientation. Here, the orientation indicator may instruct the movement of the vehicle in an orientation corresponding to a specific orientation of a coherently moving visual object. The visual object included in the orientation indicator may be a small-sized circle, but may be a Gabor patch, and the like, but is not limited thereto.

Motion coherence, which is a ratio of a consistently moving visual object included in an orientation indicator, may vary. Referring to FIG. 19, it can be seen that the motion coherence increases as the orientation indicator is further located on the right.

In the training session according to the eighth example, the device 100 may display an orientation indicator including visual objects that randomly move and visual objects that move coherently in a specific orientation on a background image including a virtual road and a virtual vehicle, and request a response related to the specific orientation from the trainee. Here, the virtual road may include a plurality of forked roads.

The rule related to the visual perceptual training applied to the training session according to the eighth example is to provide an identification task, wherein the trainee needs to identify an orientation indicator including visual objects that randomly move and visual objects that move coherently in a specific orientation, and input a correct response according to the identified specific orientation.

The rule related to visual perceptual training may be a rule requesting a response corresponding to the displayed orientation indicator including visual objects randomly moving and visual objects consistently moving in a specific orientation. Specifically, the rule related to visual perceptual training may be a rule requesting a response to move the vehicle in the same moving orientation as the specific orientation when an orientation indicator including visual objects randomly moving and visual objects consistently moving in a specific orientation is displayed.

For example, when an orientation indicator including visual objects consistently moving in the first orientation is displayed, the device 100 may request a first response to move the vehicle in the same first moving orientation as the first orientation. Also, when an orientation indicator including visual objects consistently moving in the second orientation is displayed, the device 100 may request a first response to move the vehicle in the same second moving orientation as the second orientation.

It is noted that the type of response requested by the device 100 may be changed according to rules related to visual perceptual training, such as requesting the absence of a user input from the trainee, instead of requesting the specific type of user input from the trainee.

The device 100 may check the trainee's response related to a displayed orientation indicator. For example, the device 100 may check the trainee's response with respect to visual objects that consistently move in a specific orientation included in the displayed orientation indicator. Here, the trainee's response may be related to the movement of the vehicle.

Also, the device 100 may determine whether a checked response is correct according to a rule based on the specific orientation indicator and the type of the checked response. For example, the controller 1500 may determine, as a correct response, the first response to move the vehicle in the same first moving orientation as the first orientation of the orientation indicator including visual objects consistently moving in the first orientation. Also, the controller 1500 may determine, as a correct response, the second response to move the vehicle in the same second moving orientation as the second orientation of the orientation indicator including visual objects consistently moving in the second orientation.

Also, the device 100 may change the difficulty of visual perceptual training in the training session based on the motion coherence of the orientation indicator. For example, the device 100 may decrease the difficulty of visual perceptual training in a training session by increasing the motion coherence of the orientation indicator.

Figure 20:
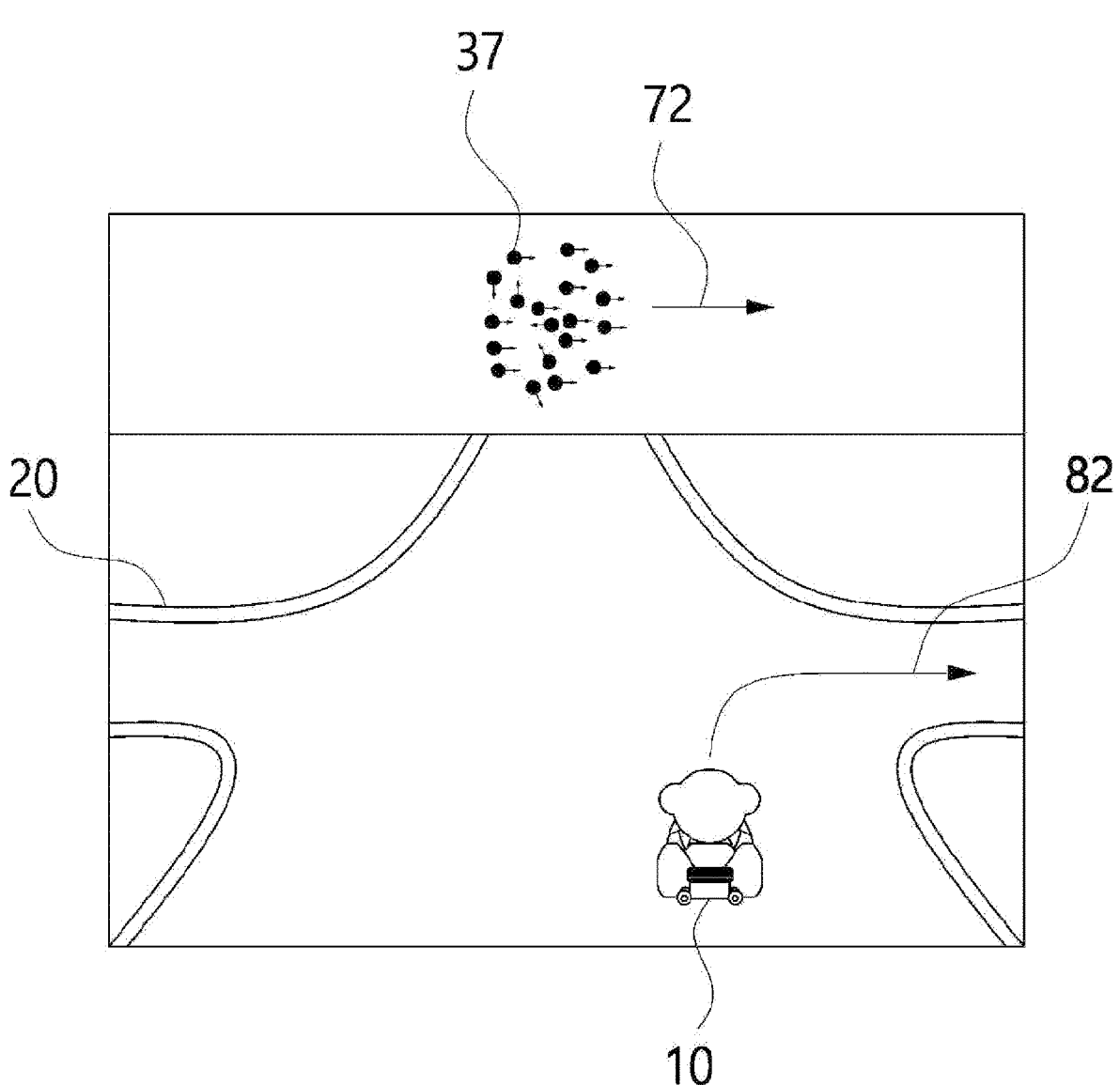
FIG. 20 is a diagram regarding an eighth example of a training session of the inventive concept.

FIG. 20 is a diagram regarding an eighth example of a training session of the inventive concept.

Referring to FIG. 20, the device 100 may display an orientation indicator 37 including visual objects moving randomly and visual objects consistently moving in a first orientation 72 on a background image including the virtual road 20 and the virtual vehicle 10. Here, the virtual road may include a plurality of forked roads.

The device 100 may request, from the trainee, a response to move the vehicle 10 in the same orientation 82 as the first orientation 72 in which the consistently moving visual objects included in the displayed orientation indicator 37 move.

Also, the device 100 may check the trainee's response in the training session. For example, the device 100 may check the type of the trainee's response with respect to the con-sistently-moving visual objects included in the displayed orientation indicator 37.

Also, the device 100 may determine whether a checked response is correct according to a rule based on the first orientation 72 and the type of the checked response.

Referring to FIG. 20, when the orientation indicator 37 including visual objects consistently moving in the first orientation 72 is displayed, the device 100 may determine, as a correct response, a response to move the vehicle 10 in the first moving orientation 82 that is the same as the first orientation 72. That is, the trainee needs to input a user input for moving the vehicle 10 into the road in the same orientation 82 as the first orientation 72 of the orientation indicator 37.

According to the inventive concept, it is possible to improve the cognitive ability of the user by using the visual perceptual training that requires a cognitive load.

According to another embodiment of the inventive concept, it is possible to arouse user's interest and improve the cognitive ability by combining visual perceptual training with navigation.

The above-described methods may be embodied in the form of program instructions that can be executed by various computer means and recorded on a computer-readable medium. The computer readable medium may include program instructions, data files, data structures, and the like, alone or in combination. Program instructions recorded on the media may be those specially designed and constructed for the purposes of the inventive concept, or they may be of the kind well-known and available to those having skill in the computer software arts. Examples of computer readable recording media include magnetic media such as hard disks, floppy disks and magnetic tape, optical media such as CD-ROMs, DVDs, and magnetic disks such as floppy disks, magneto-optical media, and hardware devices specifically configured to store and execute program instructions, such as ROM, RAM, flash memory, and the like. Examples of program instructions include not only machine code generated by a compiler, but also high-level language code that can be executed by a computer using an interpreter or the like. The hardware device described above may be configured to operate as one or more software modules to perform the operations of the present disclosure, and vice versa.

Although the embodiments have been described by the limited embodiments and the drawings as described above, various modifications and variations are possible to those skilled in the art from the above description. For example, the described techniques may be performed in a different order than the described method, and/or components of the described systems, structures, devices, circuits, etc. may be combined or combined in a different form than the described method, or other components, or even when replaced or substituted by equivalents, an appropriate result may be achieved.

Therefore, other implementations, other embodiments, and equivalents to the claims are within the scope of the following claims.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for providing visual perceptual training for improving cognitive ability, the visual perceptual training being performed by a visual perceptual training device, the method comprising:

outputting an instruction message informing a trainee of a rule related to the visual perceptual training;

providing a training session for the visual perceptual training; and storing a result in the training session for evaluating the cognitive ability of the trainee, wherein the providing of the training session includes:

sequentially displaying a plurality of orientation indicators, which are a plurality of visual objects each moving in an individual orientation;

checking a type of a response of the trainee;

determining whether the checked response is correct according to the rule including a first condition and a second condition based on an attribute of a visual object of the plurality of visual objects, a display order of the visual object, and the type of the checked response; and outputting a feedback indicating that the checked response is correct, wherein the first condition is to provide an identification task to the trainee in the training session, and request, from the trainee, a first response when the visual object having a first attribute is displayed and a second response when the visual object having a second attribute is displayed, wherein the second condition is to provide a cognitive task together with the identification task such that the training session requests a cognitive load from the trainee, and when the order of the displayed visual objects is a predetermined number, request a third response from the trainee, wherein the second condition have a higher priority than the first condition, and wherein the providing of the training session further includes:

adjusting a difficulty level of the visual perceptual training in the training session based on the trainee's response, by varying motion coherence, which is a ratio of consistently moving visual objects among the plurality of visual objects.

2. The method of claim 1, wherein the first response and the second response are a first type of a user input and a second type of user input; and wherein the third response is absence of the user input.

3. The method of claim 1, wherein the attributes of the visual object include at least one of existence or absence, contrast, size, shape, color, display time, brightness, movement, rotation, pattern, and depth.

4. The method of claim 1, wherein the visual object is related to a Gabor patch.

5. The method of claim 1, wherein the predetermined number includes at least one of a multiple of N, a number that is not the multiple of N, a number whose remainder is M when divided by N, a number whose remainder is not M when divided by N, a number whose last digit is the multiple of N, a number whose last digit is not the multiple of N, and any one of three different numbers whose last digit is less than 10, wherein N is a natural number greater than 2, and wherein M is a natural number different from N.

6. The method of claim 1, wherein the training session is provided in a background image comprising a virtual vehicle for navigation and a virtual road.

7. The method of claim 6, wherein the first response is related to movement of the vehicle in a first orientation;

wherein the second response is related to movement of the vehicle in a second orientation; and wherein the third response is related to movement of the vehicle in a third direction.

8. The method of claim 6, wherein the training session requests an additional response related to movement of the vehicle.

9. The method of claim 8, wherein the background image includes an obstacle that prevents the movement of the vehicle and, wherein the additional response is related to steering the vehicle such that the vehicle is not to collide with the obstacle.

10. A non-transitory computer-readable recording medium storing a program for executing the method of providing visual perceptual training of claim 1, in combination with a computer which is hardware.

11. A device for providing visual perceptual training comprising:

an output module; and a controller is configured to control the output module such that the output module outputs an instruction message informing a trainee of a rule related to visual perceptual training, provide a training session for the visual perceptual training, and store a result in the training session for evaluating cognitive ability of the trainee;

wherein the controller is configured to, in the training session, control the output module such that the output module sequentially displays a plurality of orientation indicators, which are a plurality of visual objects each moving in an individual orientation;

check a type of a response of the trainee;

determine whether the checked response is correct according to the rule including a first condition and a second condition based on an attribute of a visual object of the plurality of visual objects, a display order of the visual object, and the type of the checked response; and output a feedback indicating that the checked response is correct;

wherein the first condition is to provide an identification task to the trainee in the training session, and request, from the trainee, a first response when the visual object having a first attribute is displayed and a second response when the visual object having a second attribute is displayed, wherein the second condition is to provide a cognitive task together with the identification task such that the training session requests a cognitive load from the trainee, and when the order of the displayed visual objects is a predetermined number, request a third response from the trainee, wherein the second condition have a higher priority than the first condition, and wherein the controller is further configured to:

adjust a difficulty level of the visual perceptual training in the training session based on the trainee's response, by varying motion coherence, which is a ratio of consistently moving visual objects among the plurality of visual objects.

12. The device of claim 11, wherein the first response and the second response are a first type of a user input and a second type of the user input; and wherein the third response is absence of the user input.

13. The device of claim 11, wherein the attributes of the visual object include at least one of existence or absence, contrast, size, shape, color, display time, brightness, movement, rotation, pattern, and depth.

14. The device of claim 11, wherein the visual object is relate to a Gabor patch.

15. The device of claim 11, wherein the predetermined number includes at least one of a multiple of N, a number that is not the multiple of N, a number whose remainder is M when divided by N, a number whose remainder is not M when divided by N, a number whose last digit is the multiple of N, a number whose last digit is not the multiple of N, and any one of three different numbers whose last digit is less than 10, wherein N is a natural number greater than 2, and wherein M is a natural number greater than N.

16. The device of claim 11, wherein the training session is provided in a background image comprising a virtual vehicle for navigation and a virtual road.

17. The device of claim 16, wherein the first response is related to movement of the vehicle in a first orientation;

wherein the second response is related to movement of the vehicle in a second orientation; and wherein the third response is related to movement of the vehicle in a third direction.

18. The device of claim 16, wherein the training session requests an additional response related to movement of the vehicle.

19. The device of claim 18, wherein the background image includes an obstacle that prevents the movement of the vehicle and, wherein the additional response is related to steering the vehicle such that the vehicle is not to collide with the obstacle.

\* \* \* \* \*